(12) United States Patent
Yamaguchi et al.

(10) Patent No.: US 6,951,706 B2
(45) Date of Patent: *Oct. 4, 2005

(54) SULFONATE AND RESIST COMPOSITION

(75) Inventors: Satoshi Yamaguchi, Toyonaka (JP);
Yasunori Uetani, Tsukuba (JP);
Hiroshi Moriuma, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/646,710

(22) Filed: Aug. 25, 2003

(65) Prior Publication Data

US 2004/0152009 A1 Aug. 5, 2004

(30) Foreign Application Priority Data

Aug. 26, 2002 (JP) ........................................ 2002-244971
Nov. 1, 2002 (JP) ........................................ 2002-319504

(51) Int. Cl.[7] ........................... G03F 7/004; G03C 1/492
(52) U.S. Cl. .................... 430/270.1; 430/905; 430/910; 562/30; 562/41; 562/45; 562/56
(58) Field of Search .............................. 430/270.1, 905, 430/910; 562/30, 41, 45, 56

(56) References Cited

U.S. PATENT DOCUMENTS

| 5,837,420 | A | 11/1998 | Aoai et al. | |
|---|---|---|---|---|
| 2003/0068573 | A1 * | 4/2003 | Takata et al. | 430/270.1 |
| 2004/0018445 | A1 * | 1/2004 | Akita et al. | 430/270.1 |

* cited by examiner

Primary Examiner—Yvette C. Thornton
(74) Attorney, Agent, or Firm—Sughrue Mion, PLLC

(57) ABSTRACT

The present invention provides a sulfonate of the formula (I):

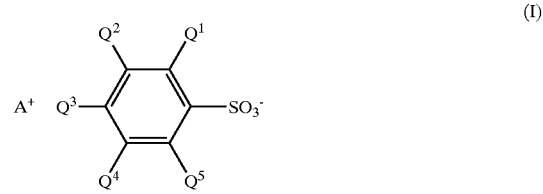

(I)

wherein $Q^1$, $Q^2$, $Q^3$, $Q^4$ and $Q^5$ each independently represent hydrogen, alkyl having 1 to 16 carbon atoms, alkoxy having 1 to 16 carbon atoms, halogen, aryl having 6 to 12 carbon atoms, aralkyl having 7 to 12 carbon atoms, cyano, sulfide, hydroxy, nitro or a group of the formula (I')

$$—COO—X—Cy^1 \qquad (I')$$

wherein X represents alkylene and at least one —$CH_2$— in the alkylene may be substituted by —O— or —S—, and $Cy^1$ represents alicyclic hydrocarbon having 3 to 20 carbon atoms, and $A^+$ represents a counter ion, with the proviso that at least one of $Q^1$, $Q^2$, $Q^3$, $Q^4$ and $Q^5$ is the group of the formula (I').

The present invention also provides a chemical amplification type positive resist composition comprising a sulfonate of the formula (I) and resin which contains a structural unit having an acid labile group and which itself is insoluble or poorly soluble in an alkali aqueous solution but becomes soluble in an alkali aqueous solution by the action of an acid.

15 Claims, No Drawings

SULFONATE AND RESIST COMPOSITION

BACKGROUND OF THE INVENTION

1. Field of the Invention

The present invention relates to a novel sulfonate and resist composition using the sameused in fine processing of semiconductors.

2. Prior Art

Semiconductor microfabrication employs a lithography process using a resist composition. In lithography, theoretically, the shorter the exposure wavelength becomes, the higher the resolution can be made, as expressed by Rayleigh's diffraction limit formula. The wavelength of an exposure light source for lithography used in the manufacture of semiconductor devices has been shortened year by year as g line having a wavelength of 436 nm, i line having a wavelength of 365 nm, KrF excimer laser having a wavelength of 248 nm and ArF excimer laser having a wavelength of 193 nm. $F_2$ excimer laser having a wavelength of 157 nm seems to be promising as the next-generation exposure light source. Further, as the exposure light source of the subsequent generation, soft X ray (EUV) having a wavelength of 13 nm or shorter has been proposed as the exposure light source following the 157 nm-wavelength $F_2$ excimer laser.

Since light sources having shorter wavelength than that of g line and i line, such as excimer laser and the like have low illumination, it is necessary to enhance the sensitivity of a resist. Consequently, there are used so-called chemical amplification type resists utilizing the catalytic action of an acid produced from a sulfonium salt and the like by exposure and containing a resin having a group being dissociated by this acid.

However, in conventionally known chemical amplification type resist compositions, there is a problem that line edge roughness occurs by generation of standing wave and the like, namely, smoothness on a pattern side wall decreases, and resultantly, uniformity of line width deteriorates.

Though it is known that the use of an acid generator including anion of benzenesulfonic acid having at least one ester group in a positive type photosensitive composition, it is still difficult to combine progress of roughness and progress of pattern shapes.

SUMMARY OF THE INVENTION

An object of the present invention is to provide a novel sulfonate and to provide a chemical amplification type resist composition comprising the above-mentioned sulfonate and a resin component, and suitable for excimer laser lithography using ArF, KrF and the like, showing excellent various resist abilities such as sensitivity, resolution and the like, and giving particularly improved line edge roughness and pattern profiles.

The present invention relates to the followings:

<1> A sulfonate of the formula (I):

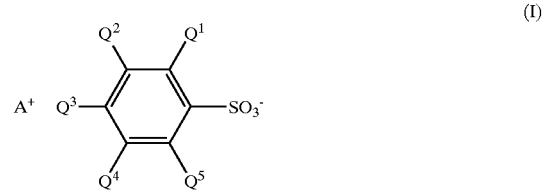

wherein $Q^1$, $Q^2$, $Q^3$, $Q^4$ and $Q^5$ each independently represent hydrogen, alkyl having 1 to 16 carbon atoms, alkoxy having 1 to 16 carbon atoms, halogen, aryl having 6 to 12 carbon atoms, aralkyl having 7 to 12 carbon atoms, cyano, sulfide, hydroxy, nitro or a group of the formula (I')

wherein X represents alkylene and at least one —$CH_2$— in the alkylene may be substituted by —O— or —S—, and $Cy^1$ represents alicyclic hydrocarbon having 3 to 20 carbon atoms, and $A^+$ represents a counter ion, with the proviso that at least one of $Q^1$, $Q^2$, $Q^3$, $Q^4$ and $Q^5$ is the group of the formula (I').

<2> The sulfonate according to <1>, wherein X in the formula (I') is alkylene.

<3> The sulfonate according to <1> or <2>, wherein $Cy^1$ in the formula (I') is cyclohexyl, 2-norbornyl, 1-adamantyl or 2-adamantyl.

<4> The sulfonate according to any one of <1> to <3> wherein $A^+$ is a counter ion of the formula (IIa)

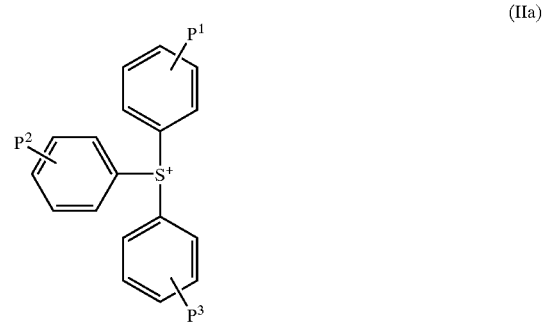

wherein $P^1$, $P^2$ and $P^3$ each independently represent hydrogen, hydroxyl, alkyl having 1 to 6 carbon atoms or alkoxy having 1 to 6 carbon atoms.

<5> The sulfonate according to any one of <1> to <3>, wherein $A^+$ is a counter ion of the formula (IIb)

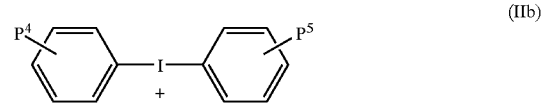

wherein $P^4$ and $P^5$ each independently represent hydrogen, hydroxyl, alkyl having 1 to 6 carbon atoms or alkoxy having 1 to 6 carbon atoms.

<6> The sulfonate according to any one of <1> to <3>, wherein $A^+$ is a counter ion of the formula (IIc)

(IIc)

wherein $P^6$ and $P^7$ each independently represent alkyl having 1 to 6 carbon atoms or cycloalkyl having 3 to 10 carbon atoms, or $P^6$ and $P^7$ bond to form divalent acyclic hydrocarbon having 3 to 7 carbon atoms which form a ring together with the adjacent $S^+$, and at least one —CH$_2$— in the divalent acyclic hydrocarbon may be substituted by —CO—, —O— or —S—; $P^8$ represents hydrogen, $P^9$ represents alkyl having 1 to 6 carbon atoms, cycloalkyl having 3 to 10 carbon atoms or aromatic ring group optionally substituted, or $P^8$ and $P^9$ bond to form 2-oxocycloalkyl together with the adjacent —CHCO—.

<7> The sulfonate according to any one of <1> to <3>, wherein $A^+$ is a counter ion of the formula (IId)

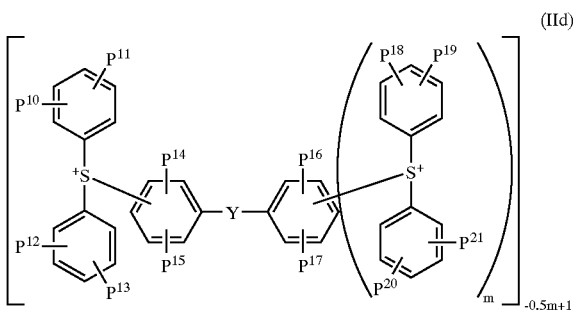

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen, hydroxyl, alkyl having 1 to 6 carbon atoms or alkoxy having 1 to 6 carbon atoms, Y represents sulfur or oxygen, and m represents 0 or 1.

<8> A chemical amplification type positive resist composition comprising a sulfonate of the formula (I)

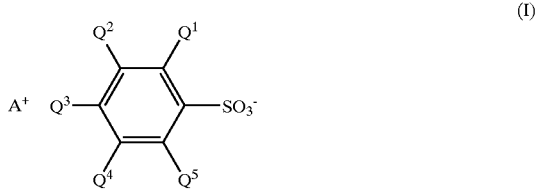

(I)

wherein $Q^1$, $Q^2$, $Q^3$, $Q^4$ and $Q^5$ each independently represent hydrogen, alkyl having 1 to 16 carbon atoms, alkoxy having 1 to 16 carbon atoms, halogen, aryl having 6 to 12 carbon atoms, aralkyl having 7 to 12 carbon atoms, cyano, sulfide, hydroxy, nitro or a group of the formula (I')

—COO—X—Cy$^1$ (I')

wherein X represents alkylene and at least one —CH$_2$— in the alkylene may be substituted by —O— or —S—, and Cy$^1$ represents alicyclic hydrocarbon having 3 to 20 carbon atoms, and $A^+$ represents a counter ion, with the proviso that at least one of $Q^1$, $Q^2$, $Q^3$, $Q^4$ and $Q^5$ is the group of the formula (I'); and resin which contains a structural unit having an acid labile group and which itself is insoluble or poorly soluble in an alkali aqueous solution but becomes soluble in an alkali aqueous solution by the action of an acid.

<9> The composition according to <8> wherein the content of the structural unit having an acid-labile group in all structural units of the resin is from 10 to 80% by mol.

<10> The composition according to <8> or <9> wherein the structural unit having an acid-labile group is a structural unit derived from 2-alkyl-2-adamantyl (meth)acrylate or 1-(1-adamantyl)-1-alkylalkyl(meth)acrylate.

<11> The composition according to any one of <8> to <10> wherein the resin contains, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl (meth)acrylate, a structural unit derived from 3,5-dihydroxy-1-adamantyl (meth)acrylate, a structural unit derived from (meth)acryloyloxy-γ-butyrolactone having a lactone ring optionally substituted by alkyl, a structural unit of the formula (VIIa) and a structural unit of the following formula (VIIb)

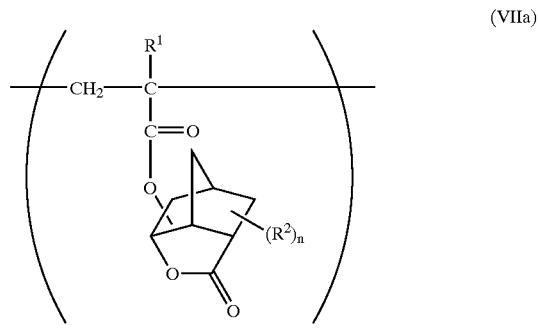

(VIIa)

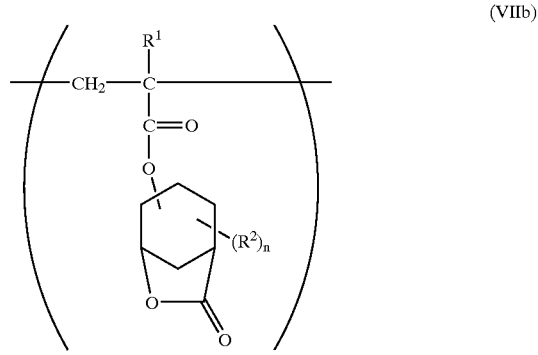

(VIIb)

wherein $R^1$ and $R^2$ each independently represent hydrogen, methyl, trifluoromethyl or, and n represents an integer of 1 to 3.

<12> The composition according to any one of <8> to <11> wherein the resin further contains a structural unit derived from 2-norbornene and a structural unit derived from an aliphatic unsaturated dicarboxylic anhydride.

<13> The composition according to any one of <8> to <11> wherein the composition further comprises basic nitrogen-containing organic compound as a quencher.

<14> The composition according to any one of <8> wherein the composition further comprises a surfactant.

<15> The composition according to any one of <8> to <14> wherein, in the formula (I), $A^+$ is a counter ion of the formula (IIa), the formula (IIb), the formula (IIc) or the formula (IId):

A counter ion of the formula (IIa)

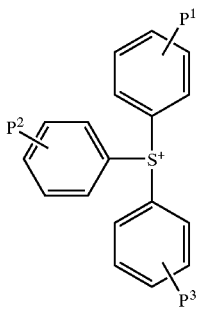
(IIa)

wherein $P^1$, $P^2$ and $P^3$ each independently represent hydrogen, hydroxyl, alkyl having 1 to 6 carbon atoms or alkoxy having 1 to 6 carbon atoms.

A counter ion of the formula (IIb)

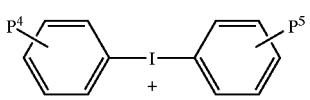
(IIb)

wherein $P^4$ and $P^5$ each independently represent hydrogen, hydroxyl, alkyl having 1 to 6 carbon atoms or alkoxy having 1 to 6 carbon atoms.

A counter ion of the formula (IIc)

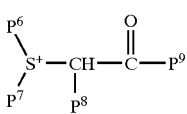
(IIc)

wherein $P^6$ and $P^7$ each independently represent alkyl having 1 to 6 carbon atoms or cycloalkyl having 3 to 10 carbon atoms, or $P^6$ and $P^7$ bond to form divalent acyclic hydrocarbon having 3 to 7 carbon atoms which form a ring together with the adjacent $S^+$, and at least one —$CH_2$— in the divalent acyclic hydrocarbon may be substituted by —CO—, —O— or —S—; $P^8$ represents hydrogen, $P^9$ represents alkyl having 1 to 6 carbon atoms, cycloalkyl having 3 to 10 carbon atoms or aromatic ring group optionally substituted, or $P^8$ and $P^9$ bond to form 2-oxocycloalkyl together with the adjacent —CHCO—.

A counter ion of the formula (IId)

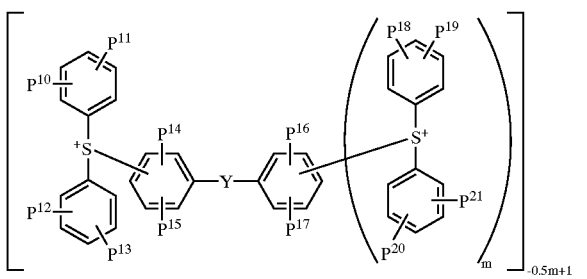
(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen, hydroxyl, alkyl having 1 to 6 carbon atoms or alkoxy having 1 to 6 carbon atoms, Y represents sulfur or oxygen, and m represents 0 or 1.

DESCRIPTION OF PREFERRED EMBODIMENTS

The present composition comprises
(1) resin which contains a structural unit having an acid labile group and which itself is insoluble or poorly soluble in an alkali aqueous solution but becomes soluble in an alkali aqueous solution by the action of an acid and
(2) the sulfonate of the formula (I).

In the sulfonate of the formula (I), $Q^1$, $Q^2$, $Q^3$, $Q^4$ and $Q^5$ each independently represent hydrogen, optionally branched alkyl having 1 to 16 carbon atoms, optionally branched alkoxy having 1 to 16 carbon atoms, halogen, aryl having 6 to 12 carbon atoms, aralkyl having 7 to 12 carbon atoms, cyano, sulfide, hydroxy, nitro or a group of the formula (I')

—COO—X—$Cy^1$ (I')

wherein X represents alkylene and at least one —$CH_2$— in the alkylene may be substituted by —O— or —S—, $Cy^1$ represents alicyclic hydrocarbon having 3 to 20 carbon atoms. Here, at least one of $Q^1$, $Q^2$, $Q^3$, $Q^4$ and $Q^5$ is the group of the formula (I').

Examples of the optionally branched alkyl having 1 to 16 carbon atoms include methyl, ethyl, propyl, isopropyl, butyl, tert-butyl, pentyl, hexyl, octyl, decyl, dodecyl, hexadecyl, and the like.

Examples of the optionally branched alkoxy having 1 to 16 carbon atoms include methoxy, ethoxy, propoxy, isopropoxy, butoxy, tert-butoxy, pentyloxy, hexyloxy, isopentyloxy, decyloxy, dodecyloxy, hexadecyloxy, and the like.

Examples of halogen include fluorine, chlorine, bromine, iodine, and the like.

Examples of aryl having 6 to 12 carbon atoms include phenyl, tolyl, methoxyphenyl, naphtyl and the like.

Examples of the aralkyl having 7 to 12 carbon atoms include benzyl, chloromethoxyphenyl, methoxybenzyl, and the like.

In the formula (I'), X represents alkylene and at least one —$CH_2$— in the alkylene may be substituted by —O— or —S—, and $Cy^1$ represents alicyclic hydrocarbon having 3 to 20 carbon atoms.

In the sulfonate of the formula (I), at least one of $Q^1$, $Q^2$, $Q^3$, $Q^4$ and $Q^5$ represents is the group of the formula (I'). When two or more of $Q^1$, $Q^2$, $Q^3$, $Q^4$ and $Q^5$ are the groups of the formula (I'), the groups of the formula (I') may be identical or different.

Examples of X include the followings:

| | |
|---|---|
| —$CH_2$— | (a-1) |
| —$CH_2$—$CH_2$— | (a-2) |
| —$CH_2$—$CH_2$—$CH_2$— | (a-3) |
| —$CH_2$—$CH_2$—$CH_2$—$CH_2$— | (a-4) |
| —$CH_2$—$CH_2$—$CH_2$—$CH_2$—$CH_2$— | (a-5) |
| —$CH_2$—$CH_2$—$CH_2$—$CH_2$—$CH_2$—$CH_2$— | (a-6) |
| —$CH_2$—$CH_2$—$CH_2$—$CH_2$—$CH_2$—$CH_2$—$CH_2$—$CH_2$— | (a-7) |
| —$CH_2$—O— | (a-8) |
| —$CH_2$—O—$CH_2$— | (a-9) |
| —$CH_2$—O—$CH_2$—$CH_2$— | (a-10) |
| —$CH_2$—$CH_2$—O—$CH_2$—$CH_2$— | (a-11) |
| —$CH_2$—S— | (a-12) |

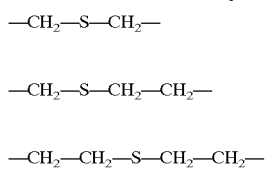
As X, (a-1) to (1-7) above are preferred.
Examples of Cy¹ include the followings:
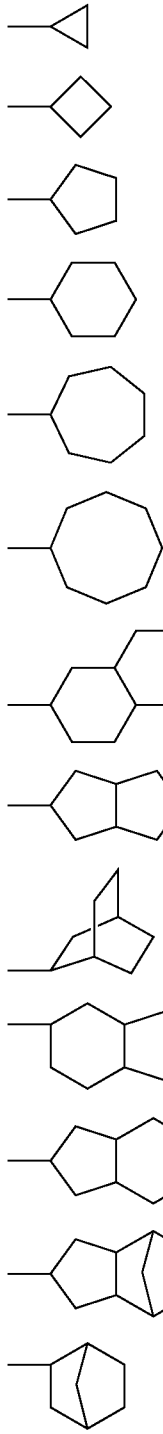
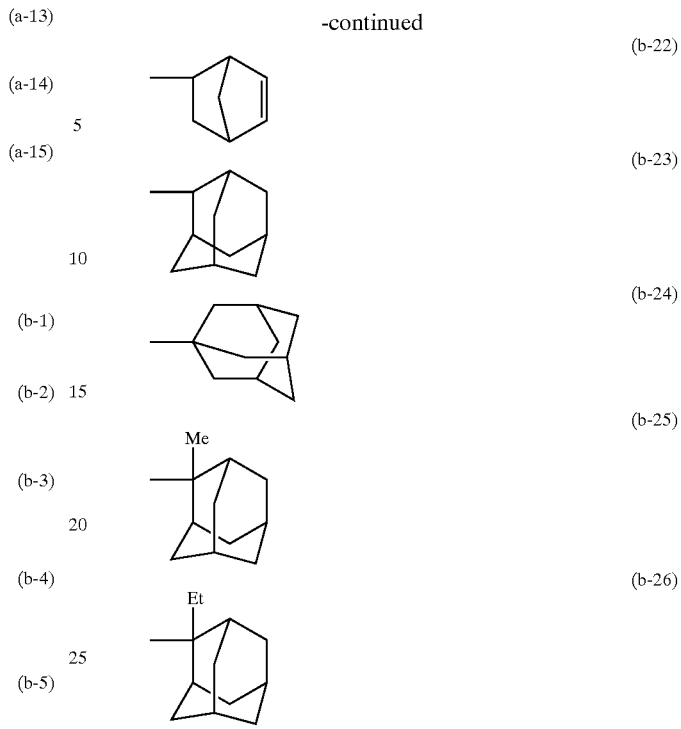
As Cy¹, cyclohexyl (b-4), 2-norbornyl (b-21), 1-adamantyl (b-24) and 2-adamantyl (b-23) are preferred.
Specific examples of the sulfonate ion in the sulfonate of the formula (I) include the followings:
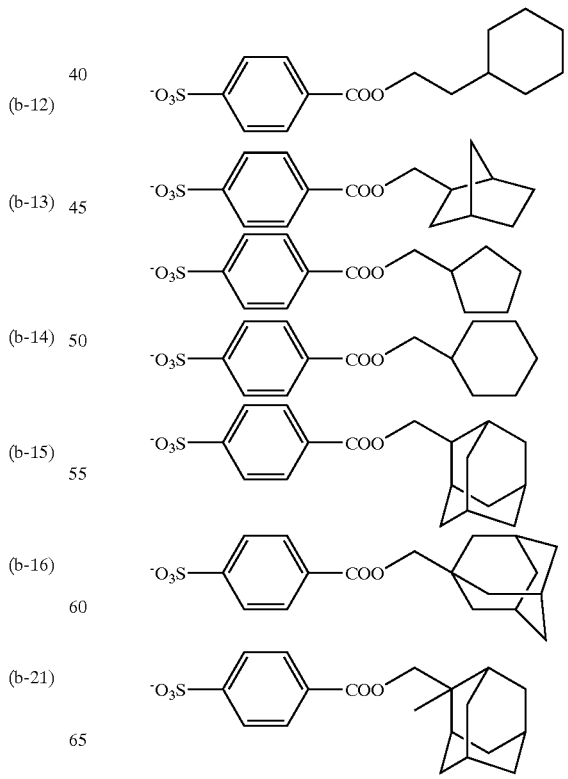

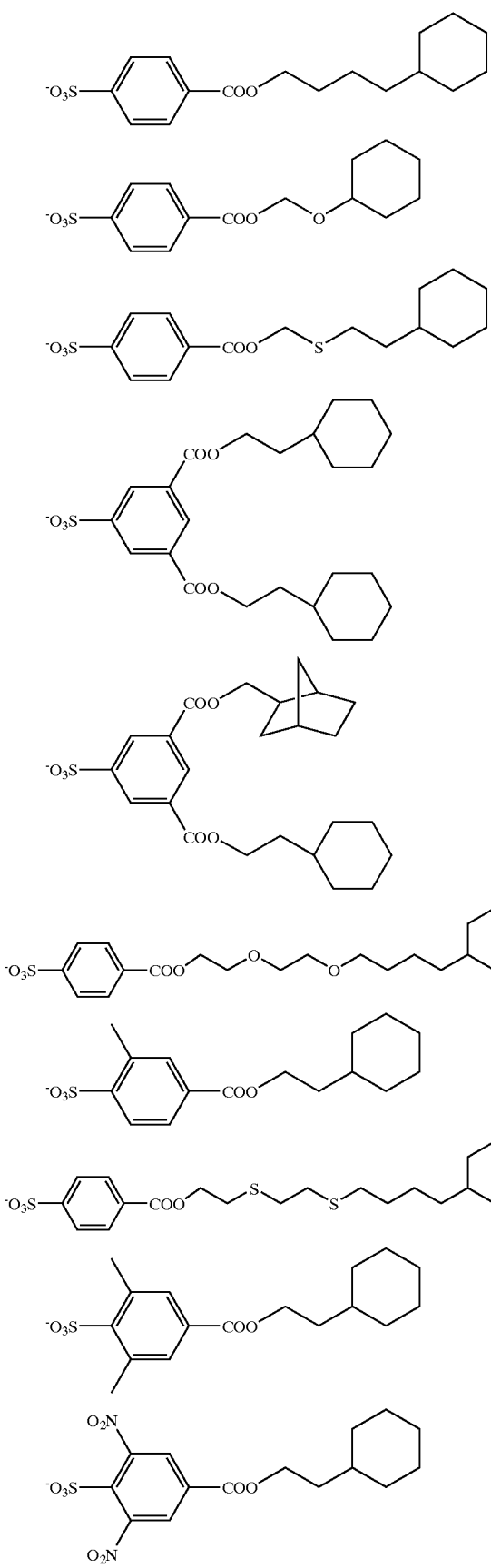
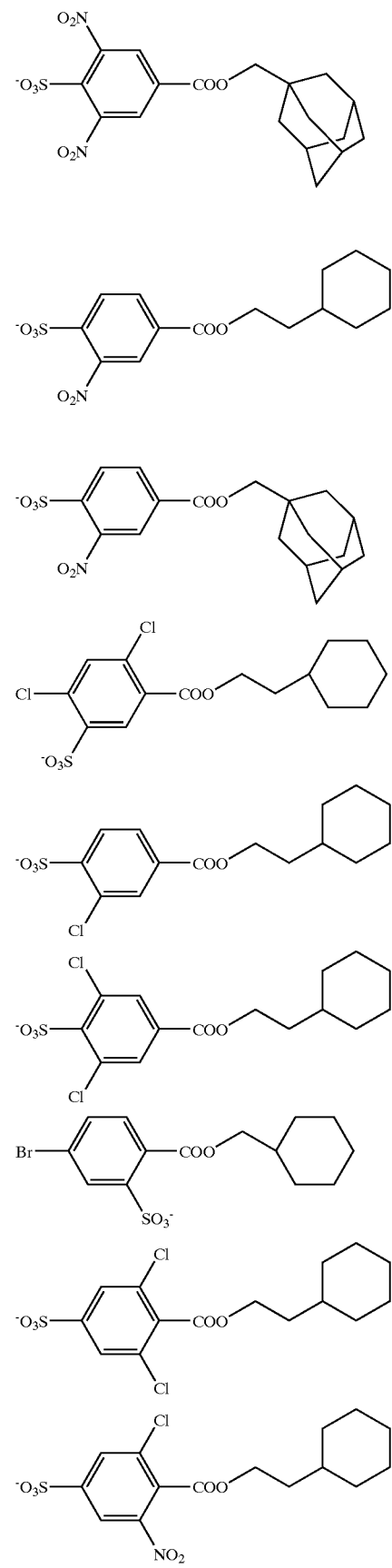

-continued
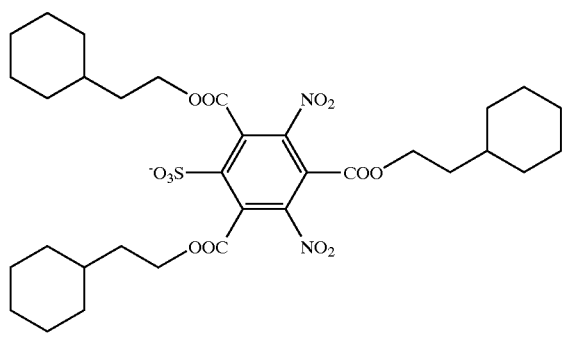
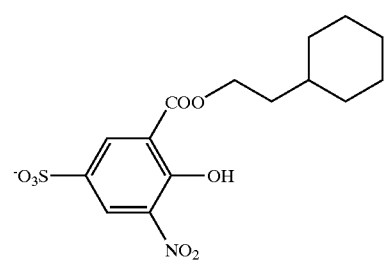
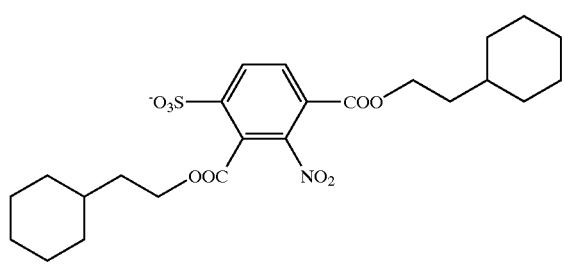
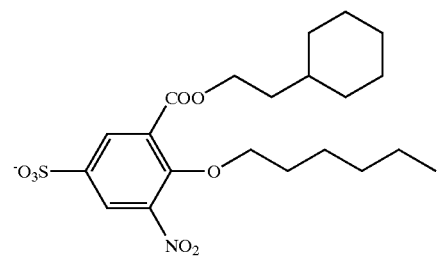
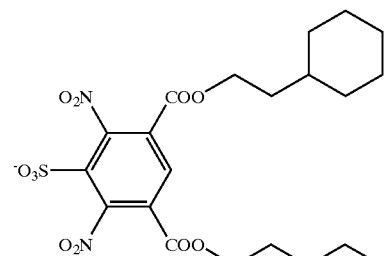
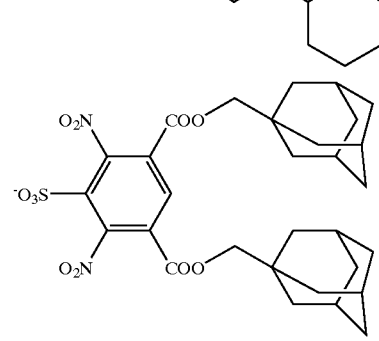
-continued
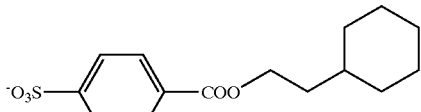
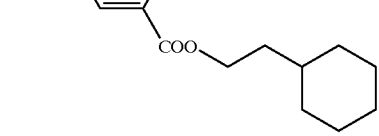
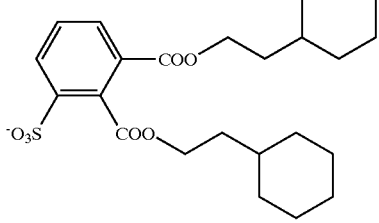
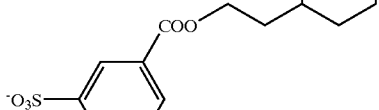
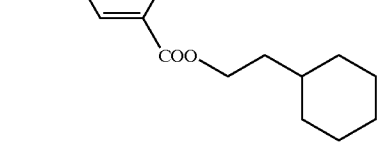
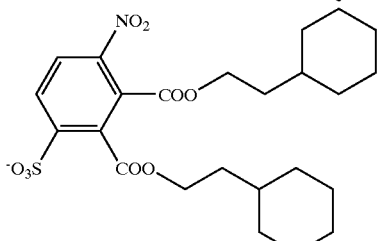
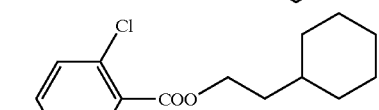
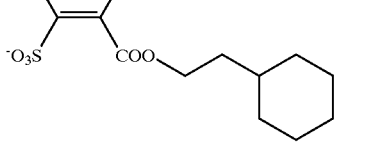
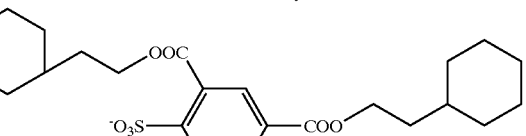
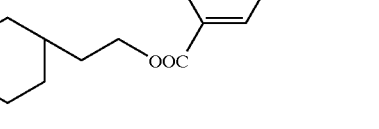
In the sulfonate of the formula (I), $A^+$ represents a counter ion and as the counter ion, a counter ions of the following formula (IIa), (IIb), (IIc) and (IId) are preferable:

A counter ion of the formula (IIa)

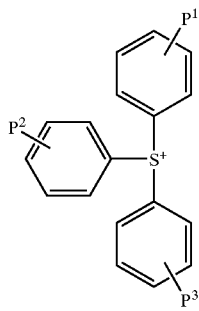

wherein $P^1$, $P^2$ and $P^3$ each independently represent hydrogen, hydroxyl, alkyl having 1 to 6 carbon atoms or alkoxy having 1 to 6 carbon atoms.

A counter ion of the formula (IIb)

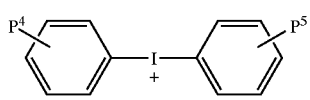

wherein $P^4$ and $P^5$ each independently represent hydrogen, hydroxyl, alkyl having 1 to 6 carbon atoms or alkoxy having 1 to 6 carbon atoms.

A counter ion of the formula (IIc):

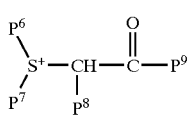

wherein $P^6$ and $P^7$ each independently represent alkyl having 1 to 6 carbon atoms or cycloalkyl having 3 to 10 carbon atoms, or $P^6$ and $P^7$ bond to form divalent acyclic hydrocarbon having 3 to 7 carbon atoms which form a ring together with the adjacent $S^+$, and at least one —CH$_2$— in the divalent acyclic hydrocarbon may be substituted by —CO—, —O— or —S—; $P^8$ represents hydrogen, $P^9$ represents alkyl having 1 to 6 carbon atoms, cycloalkyl having 3 to 10 carbon atoms or aromatic ring group optionally substituted, or $P^8$ and $P^9$ bond to form 2-oxocycloalkyl together with the adjacent —CHCO—.

A counter ion of the formula (IId):

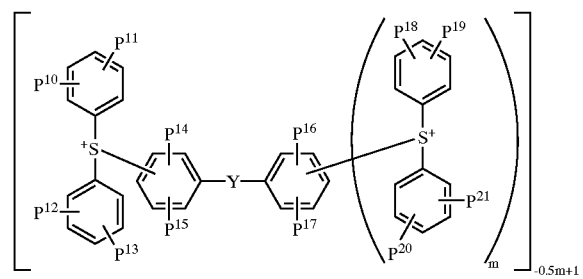

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen, hydroxyl, alkyl having 1 to 6 carbon atoms or alkoxy having 1 to 6 carbon atoms, Y represents sulfur or oxygen, and m represents 0 or 1.

In the formula (IIa), $P^1$, $P^2$ and $P^3$ each independently represent hydrogen, hydroxyl, alkyl having 1 to 6 carbon atoms or alkoxy having 1 to 6 carbon atoms, and the alkyl and alkoxy may be linear or branched in the case of 3 or more carbon atoms.

In the formula (IIb), $P^4$ and $P^5$ each independently represent hydrogen, hydroxyl, alkyl having 1 to 6 carbon atoms or alkoxy having 1 to 6 carbon atoms, and the alkyl and alkoxy may be linear or branched in the case of 3 or more carbon atoms.

In $P^1$, $P^2$, $P^3$, $P^4$ and $P^5$, specific examples of the alkyl include methyl, ethyl, propyl, isopropyl, butyl, tert-butyl, pentyl, hexyl and the like, and examples of the alkoxy include methoxy, ethoxy, propoxy, butoxy and the like.

In the formula (IIc), $P^6$ and $P^7$ each independently represent alkyl having 1 to 6 carbon atoms or cycloalkyl having 3 to 10 carbon atoms, or $P^6$ and $P^7$ bond to form divalent acyclic hydrocarbon having 3 to 7 carbon atoms which form a ring together with the adjacent $S^+$. At least one —CH$_2$— in the divalent acyclic hydrocarbon may be substituted by —CO—, —O— or —S—.

$P^8$ represents hydrogen and $P^9$ represents alkyl having 1 to 6 carbon atoms, cycloalkyl having 3 to 10 carbon atoms or aromatic ring group optionally substituted, or $P^8$ and $P^9$ bond to form 2-oxocycloalkyl together with the adjacent —CHCO—.

In $P^6$, $P^7$ and $P^9$, specific examples of the alkyl include methyl, ethyl, propyl, isopropyl, butyl, tert-butyl, pentyl, hexyl and the like, and specific examples of the cycloalkyl include cyclopropyl, cyclobutyl, cyclopentyl, cyclohexyl, cycloheptyl and the like. Specific examples of the ring group formed by adjacent $S^+$ and divalent acyclic hydrocarbon by $P^6$ and $P^7$ include pentamethylenesulfonio group, tetramethylenesulfonio group, oxybisethylenesulfonio group, and the like. In $P^9$, specific examples of the aromatic ring group include phenyl, tolyl, xylyl, naphtyl and the like. Specific examples of the 2-oxocycloalkyl formed by bonding $P^8$ and $P^9$ together with the adjacent —CHCO— include 2-oxocyclohexyl, 2-oxocyclopentyl and the like.

In the formula (IId), $P^{10}$, $P^{11}$, $P^{12}$, $P^{13}$, $P^{14}$, $P^{15}$, $P^{16}$, $P^{17}$, $P^{18}$, $P^{19}$, and $P^{21}$ each independently represent hydrogen, hydroxyl, alkyl having 1 to 6 carbon atoms or alkoxy having 1 to 6 carbon atoms. The alkyl and alkoxy may be linear or branched in the case of 3 or more carbon atoms. Specific examples of the alkyl include methyl, ethyl, propyl, isopropyl, butyl, tert-butyl, pentyl, hexyl and the like, and examples of the alkoxy include methoxy, ethoxy, propoxy, butoxy and the like. Y represents sulfur or oxygen. m represents 0 or 1.

Preferred examples of the sulfonate of the formula (I) include sulfonates of the following formulae (III), (IV), (V) and (VI):

The sulfonate of the formula (III)

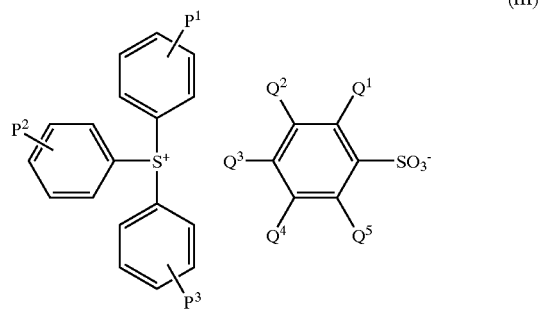

(III)

wherein $Q^1$, $Q^2$, $Q^3$, $Q^4$, $Q^5$, $P^1$, $P^2$ and $P^3$ are as defined above.

The sulfonate of the formula (IV)

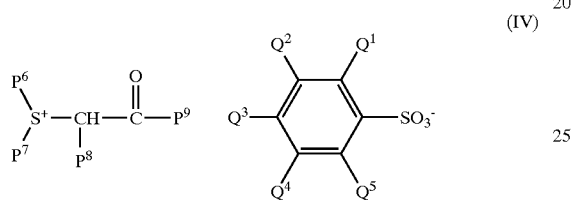

(IV)

wherein $Q^1$, $Q^2$, $Q^3$, $Q^4$, $Q^5$, $P^6$, $P^7$, $P^8$ and $P^9$ are as defined above.

The sulfonate of the formula (V)

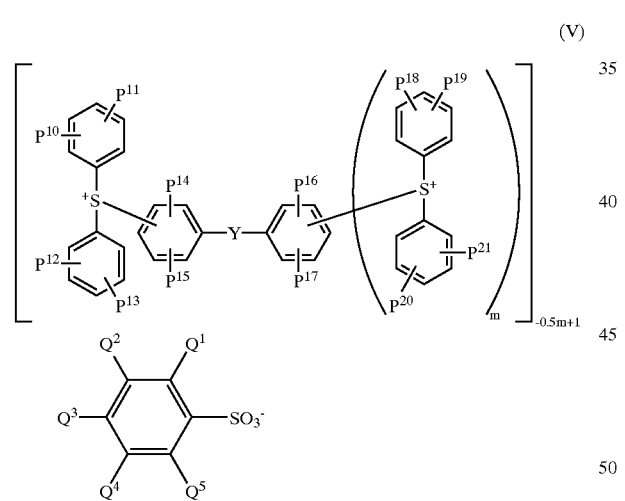

(V)

wherein $Q^1$, $Q^2$, $Q^3$, $Q^4$, $Q^5$, $P^{10}$, $P^{11}$, $P^{12}$, $P^{13}$, $P^{14}$, $P^{15}$, $P^{16}$, $P^{17}$, $P^{18}$, $P^{19}$, $P^{20}$, $P^{21}$, Y and m are as defined above.

The sulfonate of the formula (VI)

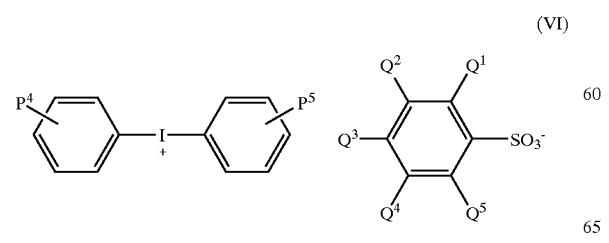

(VI)

wherein $Q^1$, $Q^2$, $Q^3$, $Q^4$, $Q^5$, $P^4$ and $P^5$ are as defined above.

Specific examples of the counter ion represented by $A^+$ in the sulfonate of the formula (I) include the followings:

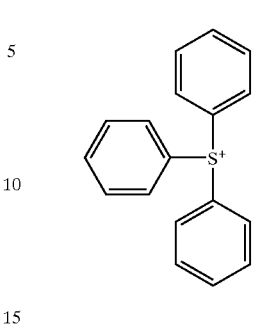

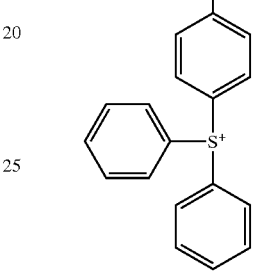

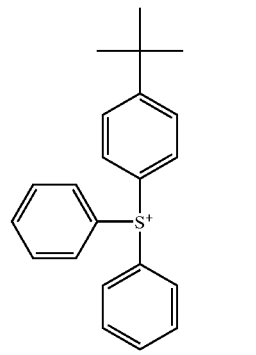

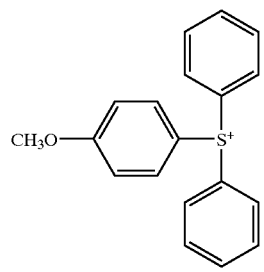

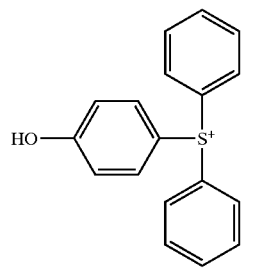

-continued
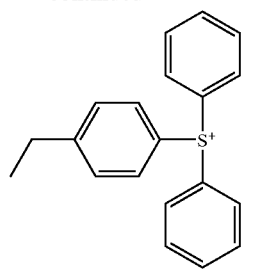
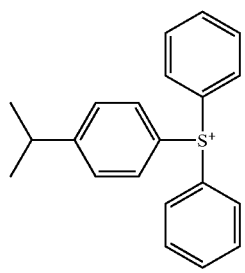
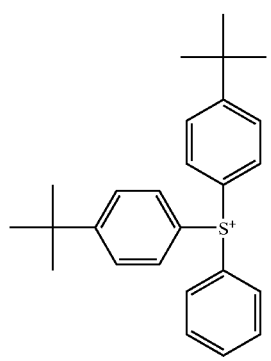
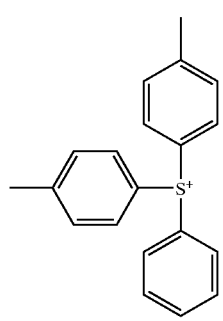
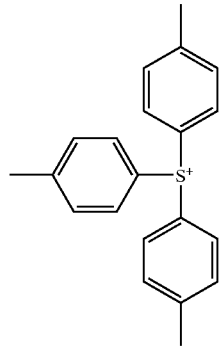
-continued
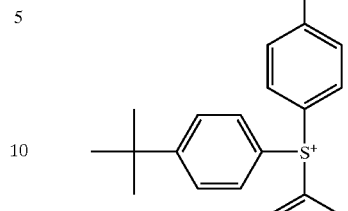
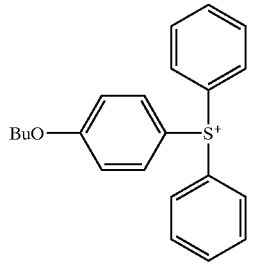
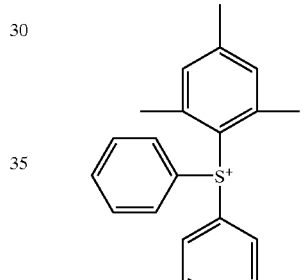
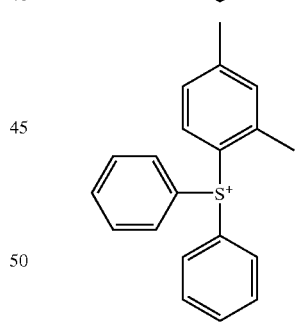
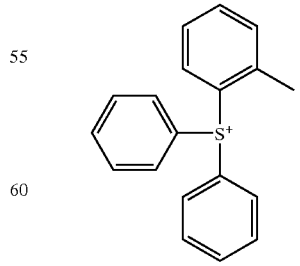
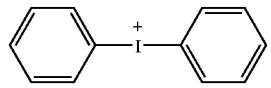

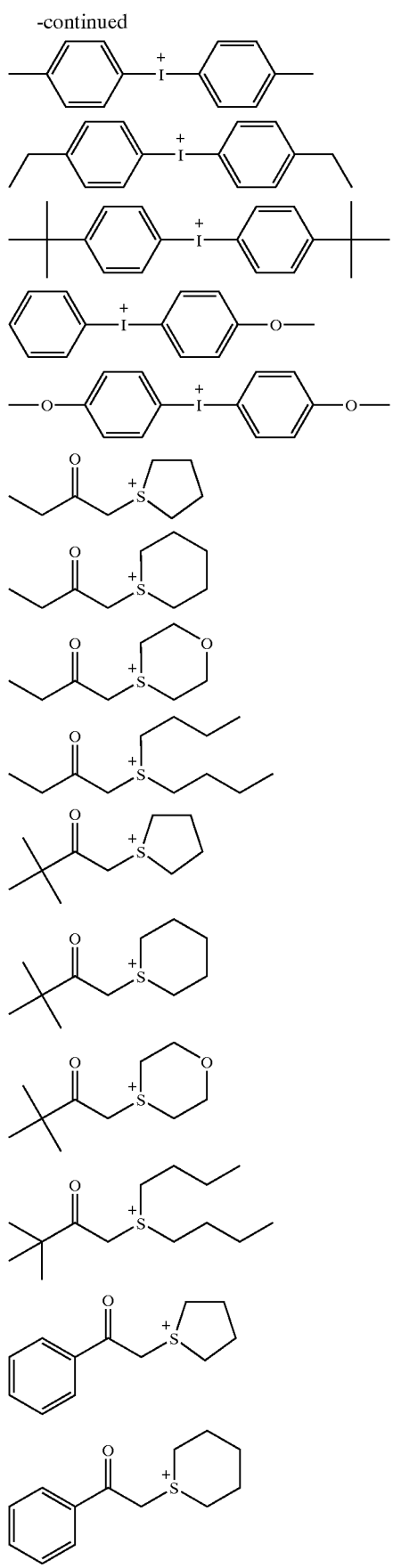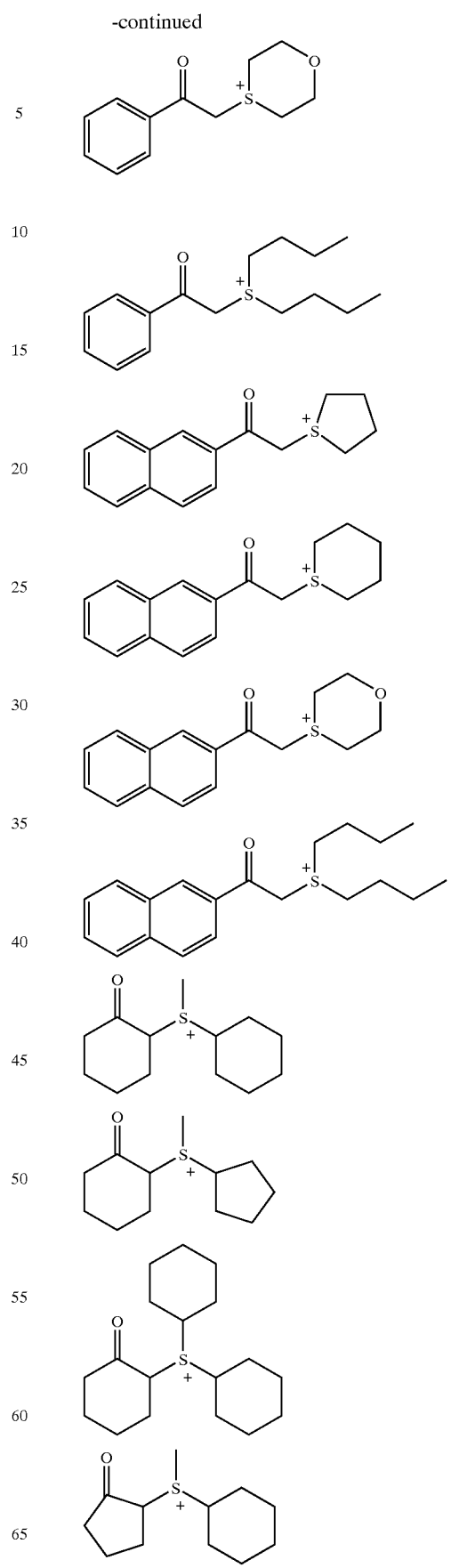

-continued
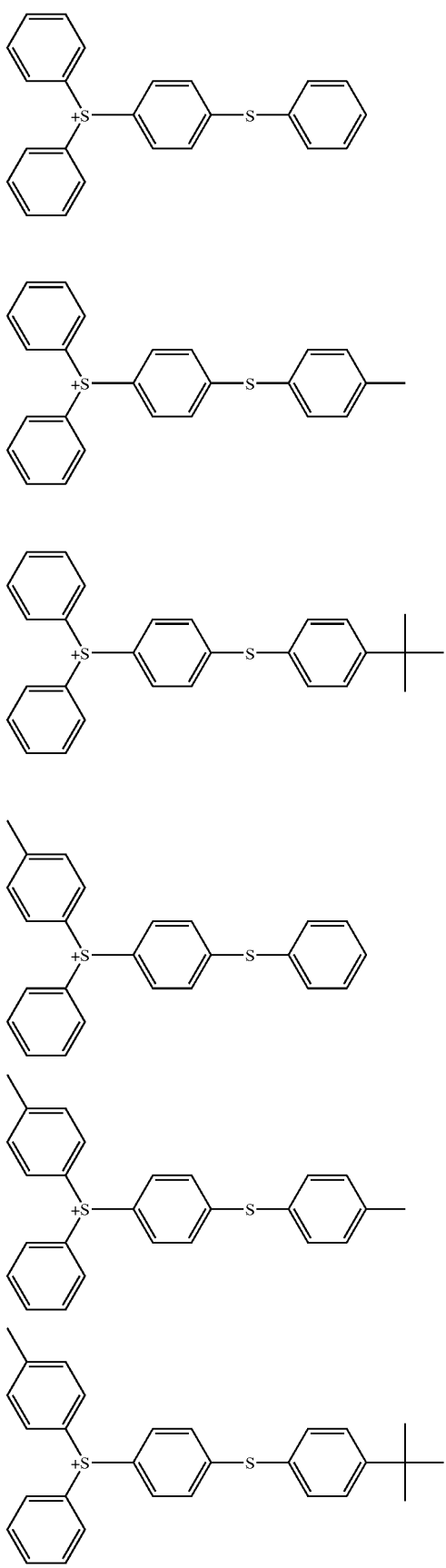
-continued
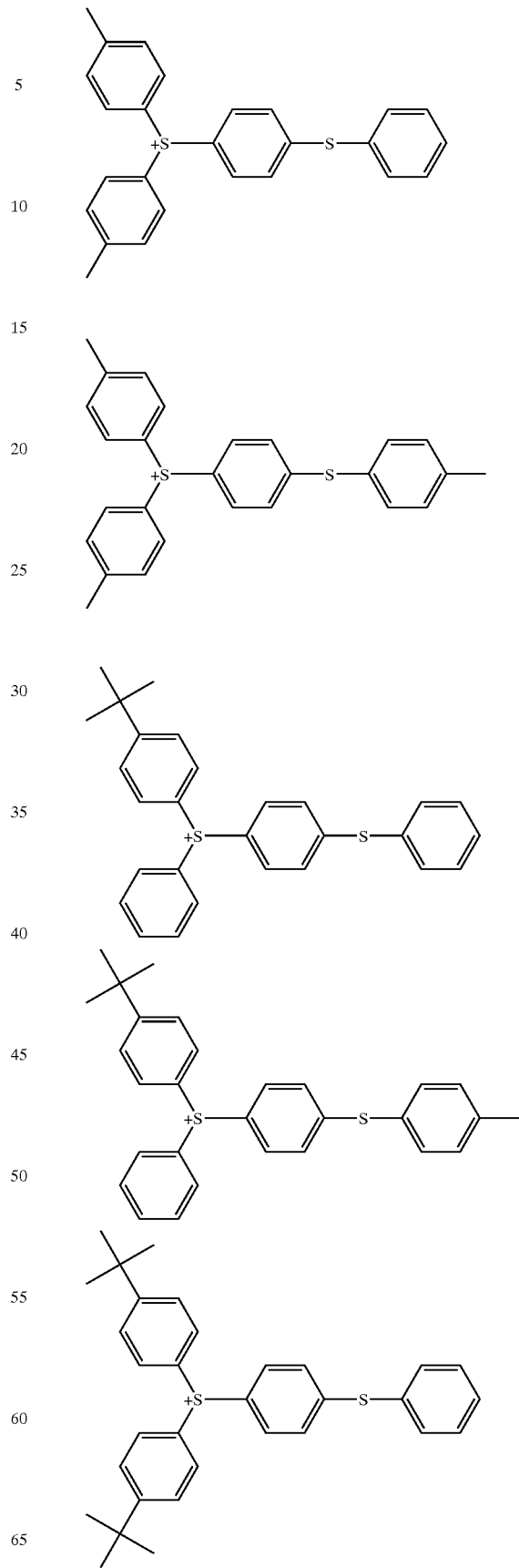

-continued
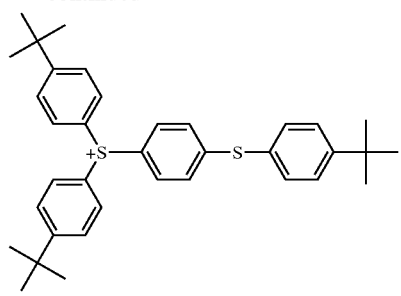
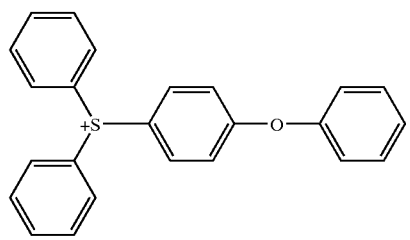
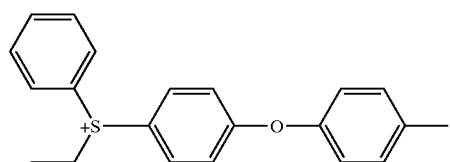
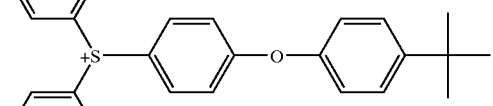
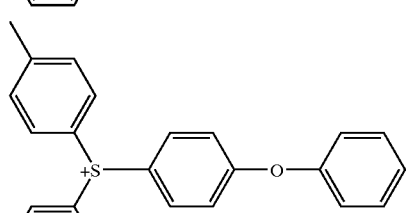
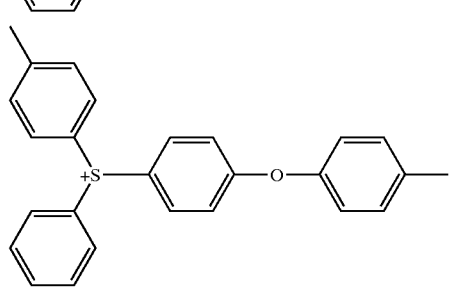
-continued
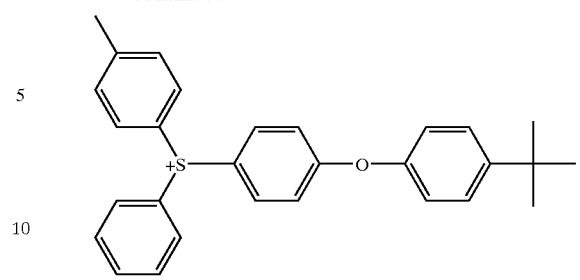
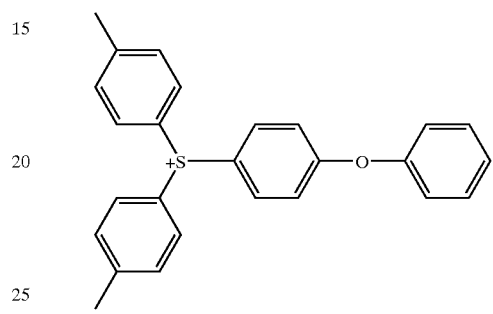
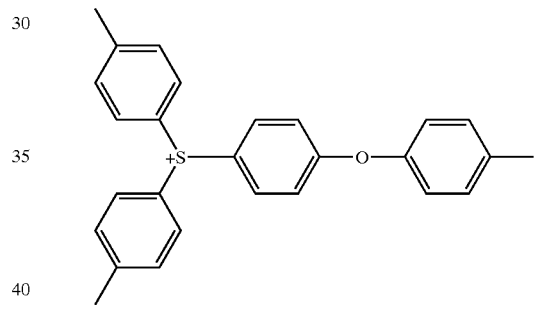
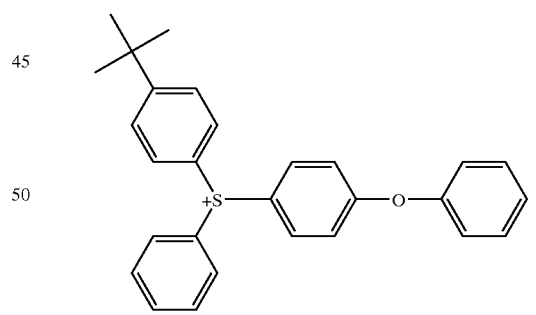
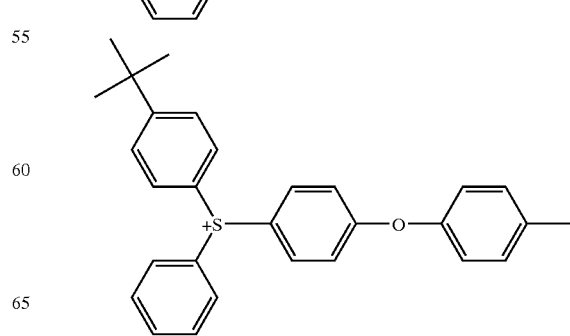

-continued
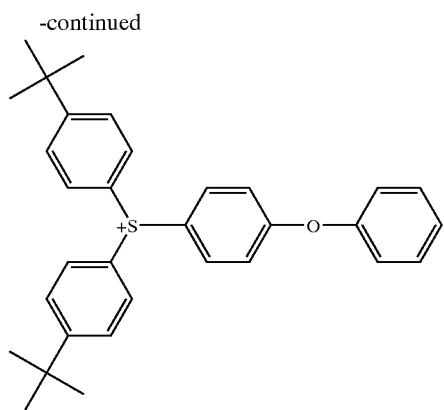
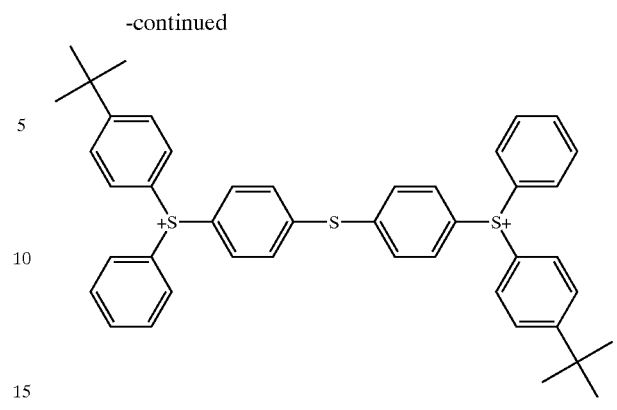
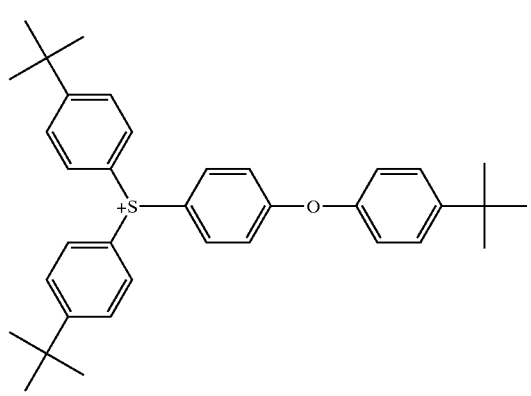
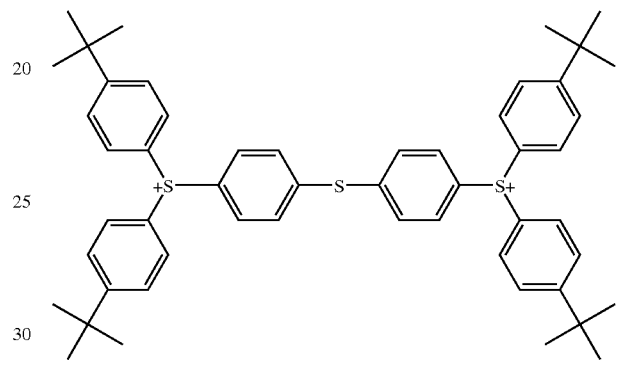
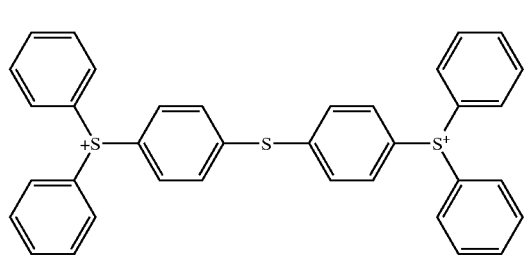
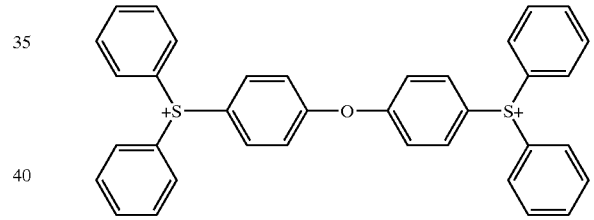
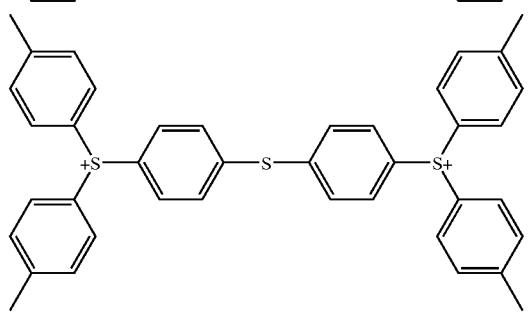
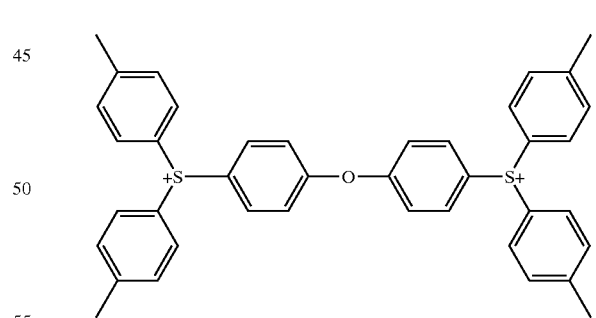
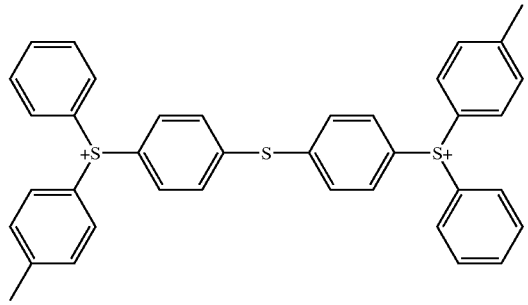
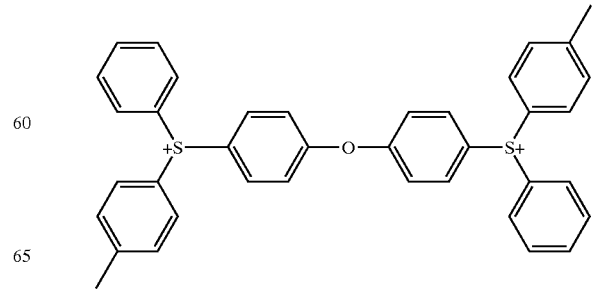

-continued

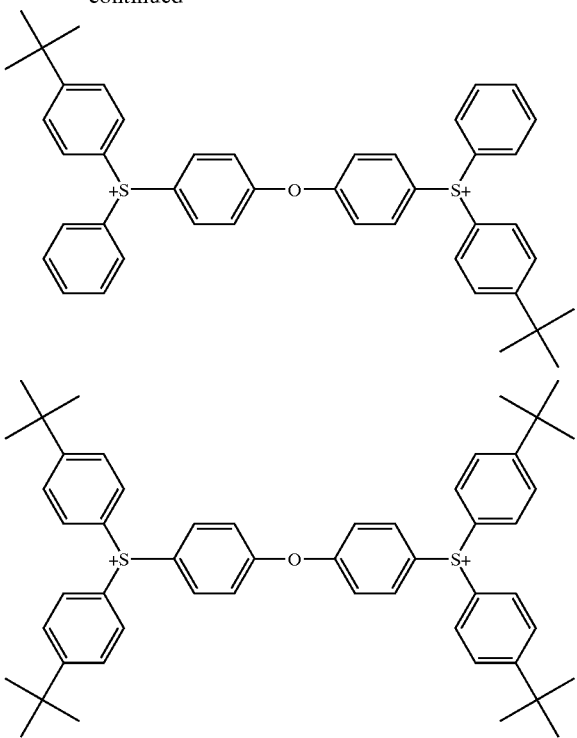

The sulfonates of the formulae (III), (IV), (V) and (VI) can be produced according to conventional methods as shown below.

The sulfonate of the formula (III) can be produced, for example, by a method reacting corresponding triphenylsulfonium bromide with silver salt of sulfonic acid having the same structure of anion part of the intended sulfonate; a method reacting corresponding aryl grignard reagent with thionyl chloride, reacting the product with triorganosilyl halide to obtain triarylsulfonium halide, and then reacting the triarylsulfonium halide with silver salt of sulfonic acid having the same structure of anion part of the intended sulfonate according to the method described in JP-H08-311018-A; and the like. The sulfonate in which $P^1$, $P^2$ or $P^3$ in the formula (III) is hydroxy, can be produced by reacting triphenylsulfonium salt having tert-butoxy on its benzene ring with sulfonic acid having the same structure of anion part of the intended sulfonate according to the method described in JP-H08-157451-A.

The sulfonate of the formula (IV) can be produced, for example, by a method reacting corresponding β-haloketone with corresponding sulfide compound to obtain corresponding sulfonium halide, and then reacting the corresuponding sulfonium halide and corresponding sulfonic acid or metal salt thereof having the same structure of anion part of the intended sulfonate applying the method described in J. Polymer Science, Polymer Chemistry Edition, Vol. 17, 2877-2892 (1979) writtern by J. V. Crivello et al.

The sulfonate of the formula (V) can be produced, for example, by a method reacting corresponding sulfonium halide with sulfonic acid or metal salt thereof having the same structure of anion part of the intended sulfonate; a method reacting corresponding diphenylsulfoxide, aryl compound (i.e. diphenyl ether, diphenylsufoxide, and the like) and perfluoroalkanesulfonic acid in the presence of trifluoroacetic anhydride to obtain corresponding sulfonium salt, converting the corresponding sulfonium salt to salt of corresponding sulfonium cation and hydroxy anion, then salt-exchanging the product with halogenide (i.e. ammonium iodide, potassium iodide and the like) to obtain salt of corresponding sulfonium cation and halogen anion, and thereafter, reacting the salt with corresponding sulfonic acid having the same structure of anion part of the intended sulfonate according to the method described in Chem. Pharm. Bull., Vol. 29, 3753 (1981).

The sulfonate of the formula (VI) can be produced, for example, by a method reacting iodosyl sulfate with corresponding aryl compound, and then adding thereto corresponding sulfonic acid having the same structure of anion part of the intended sulfonate according to a method described in J. Am. Chem. Soc., vol. 81, 342 (1959); a method adding iodine and trifluoro acetic acid to a mixture of acetic anhydride and fuming nitric acid, then reacting the reaction mixture and corresponding aryl compound, and then adding thereto corresponding sulfonic acid having the same structure of anion part of the intended sulfonate; a method reacting a mixture of corresponding aryl compound, acetic anhydride and potassium iodate by adding drop-wise concentrated sulfuric acid thereto, and then adding thereto corresponding sulfonic acid having the same structure of anion part of the intended sulfonate according to a method described in JP-H09-179302-A; and the like.

Next, resin components constituting the present composition will be explained. The resin used in the present composition contains a structural unit having an acid-labile group and the resin is insoluble or poorly soluble itself in alkali aqueous solution and shows partial dissociation of groups by the action of an acid to become soluble in alkali aqueous solution after the dissociation. The acid-labile group can be selected from conventionally known various groups.

Specifically, various carboxylate groups (—COOR) are mentioned as the acid-labile group, and examples thereof include alky carboxylate groups such as methyl carboxylate group and tert-butyl carboxylate group; acetal type carboxylate groups such as methoxymethyl carboxylate group, ethoxymethyl carboxylate group, 1-ethoxyethyl carboxylate group, 1-isobutoxyethyl carboxylate group, 1-isopropoxyethyl carboxylate group, 1-ethoxypropyl carboxylate group, 1-(2-methoxyethoxy)ethyl carboxylate group, 1-(2-acetoxyethoxy)ethyl carboxylate group, 1-[2-(1-adamantyloxy)ethoxy]ethyl carboxylate group, 1-[2-(1-adamantanecarbonyloxy)ethoxy]ethyl carboxylate group, tetrahydro-2-furyl carboxylate group and tetrahydro-2-pyranyl carboxylate group; alicyclic esters such as isobornyl carboxylate group, 2-alkyl-2-adamantyl carboxylate group, 1-(1-adamantyl)-1-alkylalkyl carboxylate group, and the like.

Monomers to be derived into structural units having such carboxylate group (—COOR) may be (meth)acryl-based monomers such as methacrylates and acrylates, or those obtained by bonding of a carboxylate group to alicyclic monomer such as norbornenecarboxylate, tricyclodecenecarboxylate and tetracyclodecenecarboxylate.

Among the above-mentioned monomers, it is preferable to use those having a bulky group containing alicyclic group such as, for example, 2-alkyl-2-adamantyl and 1-(1-adamantyl)-1-alkylalkyl, as the group dissociated by the action of an acid, since excellent resolution is obtained when used in the present composition.

Examples of such monomer containing a bulky group include 2-alkyl-2-adamantyl(meth)acrylate, 1-(1-adamantyl)-1-alkylalkyl (meth)acrylate, 2-alkyl-2-adamantyl 5-norbornene-2-carboxylate, 1-(1-adamantyl)-1-alkylalkyl 5-norbornene-2-carboxylate, and the like.

Particularly when 2-alkyl-2-adamantyl(meth)acrylate or 2-alkyl-2-adamantyl α-chloroacrylate is used as the monomer for the resin component in the present composition, excellent resolution is obtained. Typical examples of such 2-alkyl-2-adamantyl(meth)acrylate and 2-alkyl-2-adamantyl α-chloroacrylate include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate, 2-ethyl-2-adamantyl α-chloroacrylate and the like. When particularly 2-ethyl-2-adamantyl(meth) acrylate or 2-ethyl-2-adamantyl α-chloroacrylate is used for the present composition, balance between sensitivity and heat resistance is excellent. In the present invention, two or more kind of monomers having group dissociated by the action of an acid may be used together, if necessary.

2-alkyl-2-adamantyl(meth)acrylate can usually be produced by reacting 2-alkyl-2-adamantanol or metal salt thereof with an acrylic halide or methacrylic halide. 2-alkyl-2-adamantyl α-chloroacrylate can usually be produced by reacting 2-alkyl-2-adamantanol or metal salt thereof with an α-chloroacrylic halide.

The resin used for the present composition can also contain, in addition to the above-mentioned structural units having an acid-labile group, other structural units not dissociated or not easily dissociated by the action of an acid. Examples of such other structural units which can be contained include structural units derived from monomers having a free carboxyl group such as acrylic acid and methacrylic acid, structural units derived from aliphatic unsaturated dicarboxylic anhydrides such as maleic anhydride and itaconic anhydride, structural unit derived from 2-norbornene, structural unit derived from (meth) acrylonitrile, and the like.

In the case of KrF exposure, there is no problem on light absorption, and a structural unit derived from hydroxystyrene can be further contained.

Particularly, to contain, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl(meth)acrylate, a structural unit derived from 3,5-dihydroxy-1-adamantyl(meth)acrylate, a structural unit derived from (meth)acryloyloxy-γ-butyrolactone having a lactone ring optionally substituted by alkyl, a structural unit of the following formula (VIIa) and a structural unit of the following formula (VIIb), in the resin in the present composition, is preferable from the standpoint of the adhesiveness of resist to a substrate.

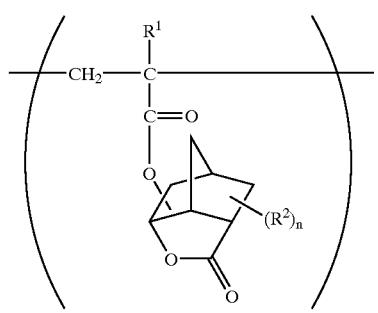

(VIIa)

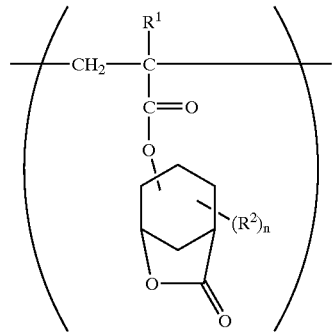

(VIIb)

In the formulae (VIIa) and (VIIb), $R^1$ and $R^2$ each independently represent hydrogen, methyl or trifluoromethyl, and n represents an integer of 1 to 3.

3-Hydroxy-1-adamantyl(meth)acrylate and 3,5-dihydroxy-1-adamantyl(meth)acrylate can be produced by, for example, reacting corresponding hydroxyadamantane with (meth)acrylic acid or its acid halide, and they are also commercially available.

Further, (meth)acryloyloxy-γ-butyrolactone can be produced by reacting α- or β-bromo-γ-butyrolactone having a lactone ring optionally substituted by alkyl with acrylic acid or methacrylic acid, or reacting α- or β-bromo-γ-butyrolactone having a lactone ring optionally substituted by alkyl with acrylic halide or methacrylic halide.

As monomers to be derived into structural units of the formulae (VIIa) and (VIIb), specifically listed are, for example, (meth)acrylates of alicyclic lactones having hydroxyl described below, and mixtures thereof, and the like. These esters can be produced, for example, by reacting corresponding alicyclic lactone having hydroxyl with (meth) acrylic acids, and the production method thereof is described in, for example, JP2000-26446-A.

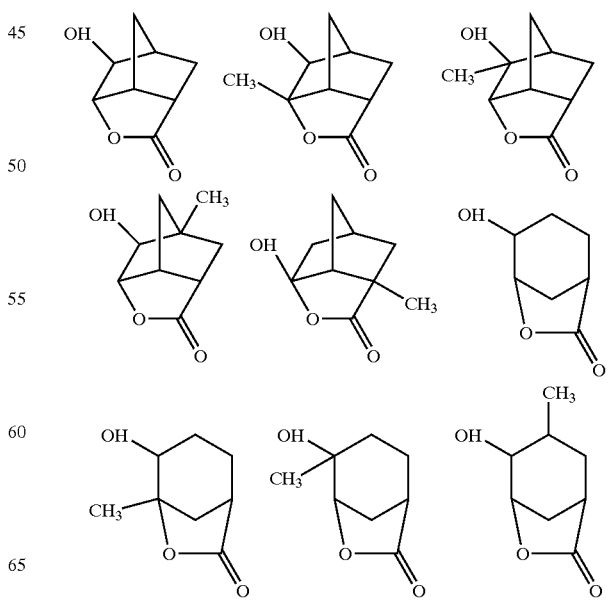

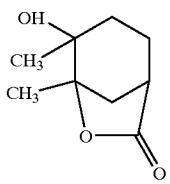

When any of the structural unit derived from 3-hydroxy-1-adamantyl (meth)acrylate, the structural unit derived from 3,5-dihydroxy-1-adamantyl (meth)acrylate, the structural unit derived from α-(meth)acryloyloxy-γ-butyrolactone, the structural unit derived from β-(meth)acryloyloxy-γ-butyrolactone and the structural unit of the formulae (VIIa) and (VIIb) is contained in the resin, not only the adhesiveness of the resist to a substrate is improved, but also the resolution of the resist is improved.

Here, examples of the (meth)acryloyloxy-γ-butyrolactone include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, β-methacryloyloxy-α-methyl-γ-butyrolactone and the like.

In the case of KrF excimer laser exposure, sufficient transmittance can be obtained even the structural unit derived from hydroxystyrene is contained in the resin. Specifically, copolymerization resins containing a structural unit derived from p- or m-hydroxystyrene as described below are listed. For obtaining such copolymerization resins, the corresponding (meth)acrylic ester monomer can be radical-polymerized with acetoxystyrene and styrene, and then the reaction mixture can be de-acetylated with an acid.

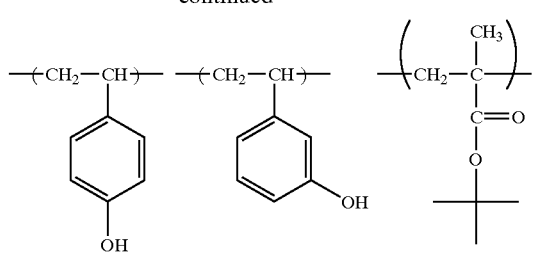

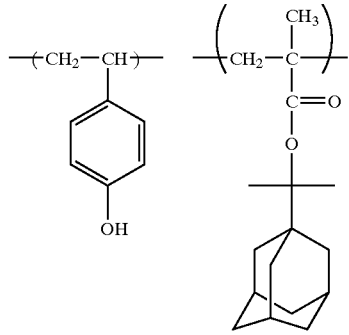

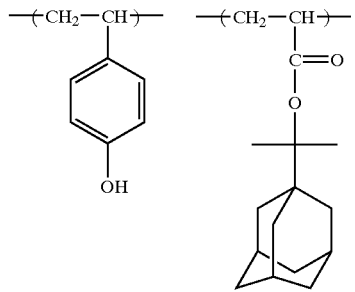

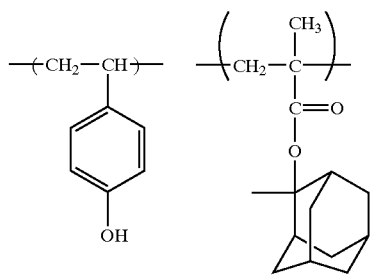

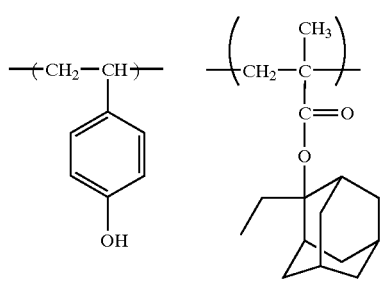

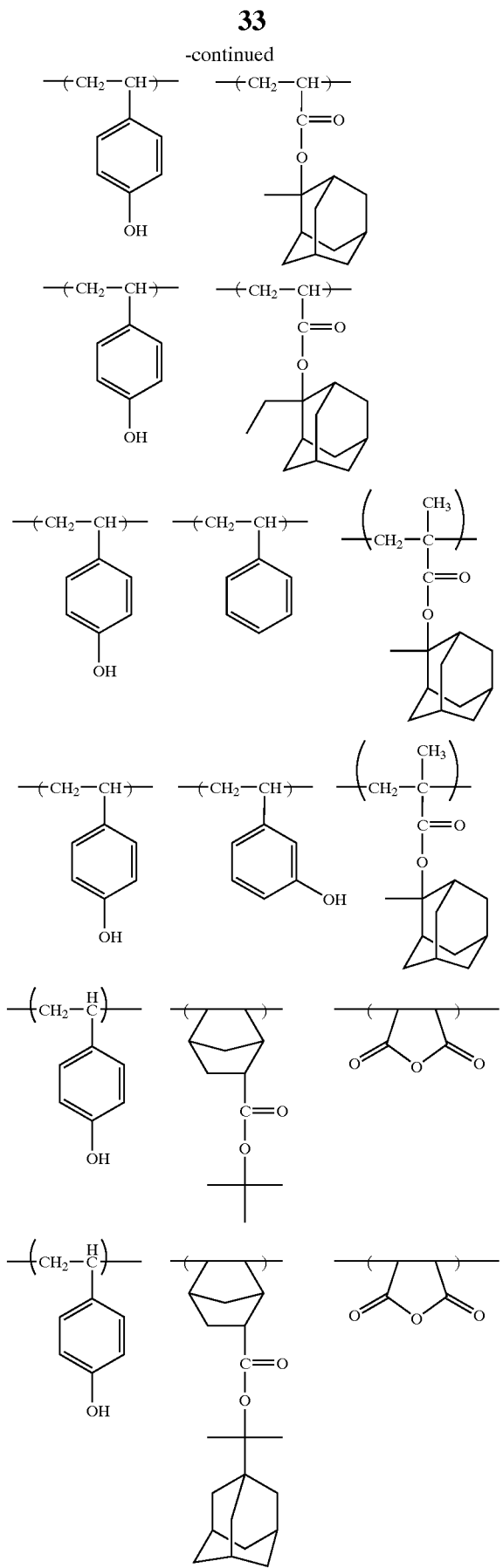

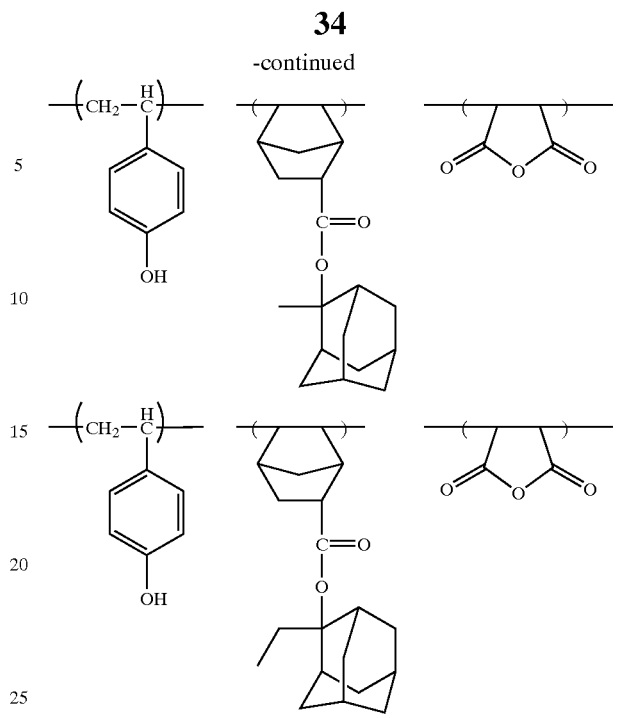

In these cases, it is advantageous from the standpoint of dry etching resistance to contain 2-alkyl-2-adamantyl or 1-(1-adamantyl)-1-alkylalkyl as the acid labile group in the resin.

The resin containing a structural unit derived from 2-norbornene shows strong structure because of alicyclic group directly present on its main chain and shows a property that dry etching resistance is excellent. The structural unit derived from 2-norbornene can be introduced into the main chain by radical polymerization using, for example, in addition to corresponding 2-norbornene, aliphatic unsaturated dicarboxylic anhydrides such as maleic anhydride and itaconic anhydride together. The structural unit derived from 2-norbornene is formed by opening of its double bond, and can be represented by the formula (VIII). The structural unit derived from maleic anhydride and the structural unit derived from itaconic anhydride which are the structural unit derived from aliphatic unsaturated dicarboxylic anhydrides are formed by opening of their double bonds, and can be represented by the formula (IX) and the formula (X), respectively.

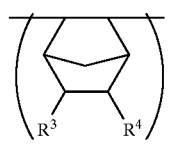

(VIII)

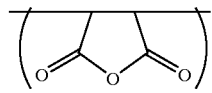

(IX)

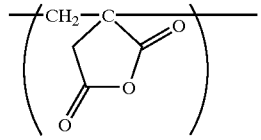

(X)

Here, $R^3$ and $R^4$ in the formula (VIII) each independently represent hydrogen, alkyl having 1 to 3 carbon atoms, hydroxyalkyl having 1 to 3 carbon atoms, carboxyl, cyano or —COOZ group in which Z represents alcohol residue, or $R^3$ and $R^4$ can bond together to form a carboxylic anhydride residue represented by —C(=O)OC(=O)—.

In $R^3$ and $R^4$, examples of the alkyl include methyl, ethyl, propyl and isopropyl, specific examples of hydroxyalkyl include hydroxymethyl, 2-hydroxyethyl and the like.

In $R^3$ and $R^4$, —COOZ group is an ester formed from carboxyl, and as the alcohol residue corresponding to Z, for example, optionally substituted alkyls having about 1 to 8 carbon atoms, 2-oxooxolan-3- or -4-yl and the like are listed, and as the substituent on the alkyl, hydroxyl, alicyclic hydrocarbon residues and the like are listed.

Specific examples of —COOZ include methoxycarbonyl, ethoxycarbonyl, 2-hydroxyethoxycarbonyl, tert-butoxycarbony, 2-oxooxalan-3-yloxycarbonyl, 2-oxooxalan-4-yloxycarbonyl, 1,1,2-trimethylpropoxycarbonyl, 1-cyclohexyl-1-methylethoxycarbonyl, 1-(4-methylcyclohexyl)-1-methylethoxycarbonyl, 1-(1-adamantyl)-1-methylethoxycarbonyl and the like.

Specific examples of the monomer used to derive the structural unit represented by the formula (VIII) may include the followings;
2-norbornene,
2-hydroxy-5-norbornene,
5-norbornen-2-carboxylic acid,
methyl 5-norbornen-2-carboxylate,
t-butyl 5-norbornen-2-carboxylate,
1-cyclohexyl-1-methylethyl 5-norbornen-2-carboxylate,
1-(4-methylcyclohexyl)-1-methylethyl 5-norbornen-2-carboxylate,
1-(4-hydroxycyclohexyl)-1-methylethyl 5-norbornen-2-carboxylate,
1-methyl-1-(4-oxocyclohexyl)ethyl 5-norbornen-2-carboxylate,
1-(1-adamantyl)-1-methylethyl 5-norbornen-2-carboxylate,
1-methylcyclohexyl 5-norbornen-2-carboxylate,
2-methyl-2-adamantyl 5-norbornen-2-carboxylate,
2-ethyl-2-adamantyl 5-norbornen-2-carboxylate,
2-hydroxyethyl 5-norbornen-2-carboxylate,
5-norbornen-2-methanol,
5-norbornen-2,3-dicarboxylic acid anhydride, and the like.

The resin used in the present composition preferably contains structural unit(s) having an acid-labile group generally in a ratio of 10 to 80% by mol in all structural units of the resin though the ratio varies depending on the kind of radiation for patterning exposure, the kind of an acid-labile group, and the like.

When the structural units particularly derived from 2-alkyl-2-adamantyl (meth)acrylate or 1-(1-adamantyl)-1-alkylalkyl(meth)acrylate are used as the acid-labile group, it is advantageous that the ratio of the structural units is 15% by mol or more in all structural units of the resin.

When, in addition to structural units having an acid-labile group, other structural units not easily dissociated by the action of an acid, for example, a structural unit derived from 3-hydroxy-1-adamantyl(meth)acrylate, a structural units derived from 3,5-dihydroxy-1-adamantyl(meth)acrylate or α-(meth)acryloyloxy-γ-butyrolactone, a structural units derived from β-(meth)acryloyloxy-γ-butyrolactone, a structural unit of the formula (VIIa) or (VIIb), a structural unit derived from hydroxystyrene, a structural unit of the formula (VIII), a structural unit derived from maleic anhydride of the formula (IX) which is a structural unit derived from an aliphatic unsaturated dicarboxylic anhydride, a structural unit derived from itaconic anhydride of the formula (X) and the like are contained, it is preferable that the sum of these structural units is in the range of 20 to 90% by mol based on all structural units of the resin.

When 2-norbornenes and aliphatic unsaturated dicarboxylic anhydride are used as copolymerization monomer, it is preferable to use them in excess amount in view of a tendency that these are not easily polymerized.

In the present composition, performance deterioration caused by inactivation of acid which occurs due to post exposure delay can be diminished by adding basic compounds, particularly, basic nitrogen-containing organic compounds, for example, amines as a quencher.

Specific examples of such basic nitrogen-containing organic compounds include the ones represented by the following formulae:

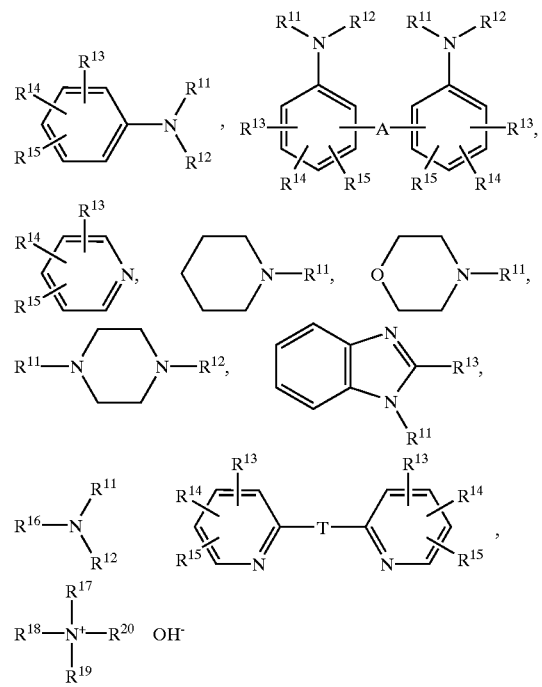

Wherein $R^{11}$ and $R^{12}$ represent each independently hydrogen, alkyl, cycloalkyl or aryl. The alkyl preferably has about 1 to 6 carbon atoms, the cycloalkyl preferably has about 5 to 10 carbon atoms, and the aryl preferably has about 6 to 10 carbon atoms. Furthermore, at least one hydrogen on the alkyl, cycloalkyl or aryl may each independently be substituted by hydroxyl, amino, or alkoxy having 1 to 6 carbon atoms. At least one hydrogen on the amino may each independently be substituted by alkyl having 1 to 4 carbon atoms.

$R^{13}$, $R^{14}$ and $R^{15}$ each independently represent hydrogen, alkyl, cycloalkyl, aryl or alkoxy. The alkyl preferably has about 1 to 6 carbon atoms, the cycloalkyl preferably has about 5 to 10 carbon atoms, the aryl preferably has about 6 to 10 carbon atoms, and the alkoxy preferably has about 1 to 6 carbon atoms. Furthermore, at least one hydrogen on the alkyl, cycloalkyl, aryl or alkoxy may each independently be substituted by hydroxyl, amino, or alkoxy having 1 to 6 carbon atoms. At least one hydrogen on the amino may be substituted by alkyl having 1 to 4 carbon atoms.

$R^{16}$ represents alkyl or cycloalkyl. The alkyl preferably has about 1 to 6 carbon atoms, and the cycloalkyl preferably has about 5 to 10 carbon atoms. Furthermore, at least one hydrogen on the alkyl or cycloalkyl may each independently be substituted by hydroxyl, amino, or alkoxy having 1 to 6 carbon atoms. At least one hydrogen on the amino may be substituted by alkyl having 1 to 4 carbon atoms.

$R^{17}$, $R^{18}$, $R^{19}$ and $R^{20}$ each independently represent alkyl, cycloalkyl or aryl. The alkyl preferably has about 1 to 6 carbon atoms, the cycloalkyl preferably has about 5 to 10 carbon atoms, and the aryl preferably has about 6 to 10 carbon atoms. Furthermore, at least one hydrogen on the alkyl, cycloalkyl or aryl may each independently be substituted by hydroxyl, amino, or alkoxy having 1 to 6 carbon atoms. At least one hydrogen on the amino may each independently be substituted by alkyl having 1 to 4 carbon atoms.

T represents alkylene, carbonyl, imino, sulfide or disulfide. The alkylene preferably has about 2 to 6 carbon atoms.

Moreover, among $R^{11}$–$R^{20}$, in regard to those which can be straight-chained or branched, either of these may be permitted.

Examples of such compounds include hexylamine, heptylamine, octylamine, nonylamine, decylamine, aniline, 2-, 3- or 4-methylaniline, 4-nitroaniline, 1- or 2-naphtylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenyl amine, triethylamine, trimethyl amine, tripropylamine, tributylamine, tripentylamine, trihexylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-isopropylaniline, imidazole, pyridine, 4-methylpyridine, 4-methylmidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, phenyltrimethylammonium hydroxide, 3-trifluoromethylphenyltrimethylammonium hydroxide, (2-hydroxyethyl)trimethylammonium hydroxide (so-called "cholline"), and the like.

Furthermore, hindered amine compounds having piperidine skeleton as disclosed in JP-A-H11'-52575 can be used as quencher.

It is preferable that the present composition contains resin in an amount of about 80 to 99.9% by weight and the sufonate of the formula (I) in an amount of 0.1 to 20% by weight based on the total solid content of the present composition.

When basic compound is used as a quencher, it is preferable that the basic compound is contained in an amount of about 0.01 to 1% by weight based on the total solid content of the present composition.

The present composition can contain, if necessary, various additives in small amount such as a sensitizer, solution suppressing agent, other resins, surfactant, stabilizer, dye and the like, as long as the effect of the present invention is not prevented.

The present composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used. In the present invention, the total solid content means total content exclusive of solvents.

Examples thereof include glycol ether esters such as ethylcellosolve acetate, methylcellosolve acetate and propylene glycol monomethyl ether acetate; esters such as ethyl lactate, butyl lactate, amyl lactate and ethyl pyruvate and the like; ketones such as acetone, methyl isobutyl ketone, 2-heptanone and cyclohexanone; cyclic esters such as γ-butyrolactone, and the like. These solvents can be used each alone or in combination of two or more.

A resist film applied onto the substrate and then dried is subjected to exposure for patterning, then heat-treated for facilitating a deblocking reaction, and thereafter developed with an alkali developer. The alkali developer used here may be any one of various alkaline aqueous solutions used in the art, and generally, an aqueous solution of tetramethylammonium hydroxide or (2-hydroxyethyl)trimethylammonium hydroxide (commonly known as "choline") is often used.

The present invention will be described more specifically by way of examples, which are not construed to limit the scope of the present invention. The "%" and "part(s)" used to represent the content of any component and the amount of any material used in the following examples are on a weight basis unless otherwise specifically noted. The weight-average molecular weight of any material used in the following examples is a value found by gel permeation chromatography using styrene as a standard reference material.

ACID GENERATOR SYNTHESIS EXAMPLE 1

Synthesis of Acid Generator B1

Into a flask was charged 6 parts of 5-sulfoisophtalic acid and 50 parts of cyclohexaneethanol, and the mixture was stirred at 135 to 140° C. for 9 hours. After cooling, to this was added 50 parts of dimethylsulfoxide, 10 parts of methanol and and 200 parts of n-heptane, the mixture was stirred and settled to give two separate layers. After separating the bottom layer from the upper layer, the bottom layer was washed with n-heptane twice. The mixture obtained by correcting the upper layer and two washed n-heptane was concentrated by evaporating n-heptane and methanol. To the solution obtained was added 3.0 parts of silver oxide, and the mixture was stirred for 16 hours at room temperature. After filtration, to the filtrate was added dropwise the mixture of 8.67 parts of p-tolyldiphenylsulfonium iodide and 86.7 parts of methanol, and then the mixture was stirred for 16 hours at room temperature. After filtration, to the filtrate was 200 parts of ethyl acetate, and washed with 100 parts of water 5 times. The organic layer obtained was concentrated. The concentrate was washed with 200 parts of n-heptane and then concentrated, and the washing and concentration was repeated twice. The concentrate was washed with another 200 parts of n-heptane and then washed, concentrated and filtrated to obtain 6.24 parts of pale yellow crystals.

It was confirmed that the structure of the crystals was the following formula by NMR ("GX-270" manufactured by JEOL Ltd.) and mass spectrometry (LC analyser is No.1100 manufactured by HP, MASS analyser is LC/MSD manufactured by HP).

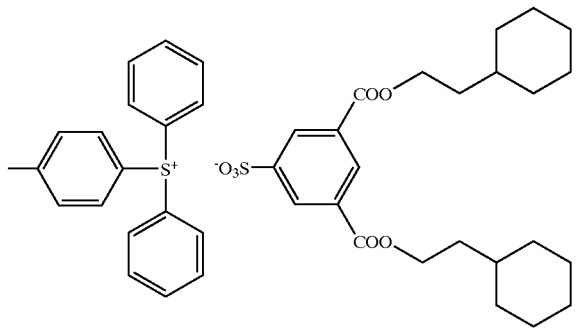

$^1$H-NMR (chloroform-d, internal standard substance: tetramethylsilane): δ (ppm) 0.94–1.00 (m, 4H); 1.14–1.26 (m, 6H); 1.41–1.44 (m, 2H); 1.62–1.76 (m, 14); 2.44 (s, 3H); 4.33 (t, 4H); 7.46 (d, 2H); 7.65–7.77 (m, 12H); 8.61 (s, 1H) 8.77 (d, 2H) MS (ESI (+) Spectrum): M+ 277.2 MS (ESI (−) Spectrum): M− 465.2

ACID GENERATOR SYNTHESIS EXAMPLE 2

Synthesis of Acid Generator B2

Into a flask was charged 20.0 parts of 5-sulfoisophtalic acid, 18.9 parts of 2-norbornanemethanol and 80.0 parts of toluene, and the mixture was refluxed while dehydration for 4 hours. After cooling, the reaction mixture was charged to 500 parts of n-heptane, and then stirred at for an hour. The resulting mixture was filtrated and the solid obtained was dried under reduced pressure to obtain 24.4 parts of diester. 15 parts of the diester was dissolved in 150 parts of methanol, and to the solution was added 4.5 parts of silver oxide, and the mixture was stirred for 16 hours at room temperature. After filtration, to the filtrate was added dropwise the mixture of 13.1 parts of p-tolyldiphenylsulfonium iodide and 131 parts of methanol, and then the mixture was stirred for 12 hours at room temperature. After filtration, to the filtrate was 200 parts of ethyl acetate, and washed with 100 parts of water 5 times. The organic layer obtained was filtrated and then concentrated. The concentrate was washed with 300 parts of n-heptane and then concentrated, and the washing and concentration was repeated seven times. The concentrate was washed with another 300 parts of n-heptane and then washed, concentrated completely to obtain 15.0 parts of brown crystals.

It was confirmed that the structure of the crystals was the following formula by NMR ("GX-270" manufactured by JEOL Ltd.) and mass spectrometry (LC analyser is No.1100 manufactured by HP, MASS analyser is LC/MSD manufactured by HP).

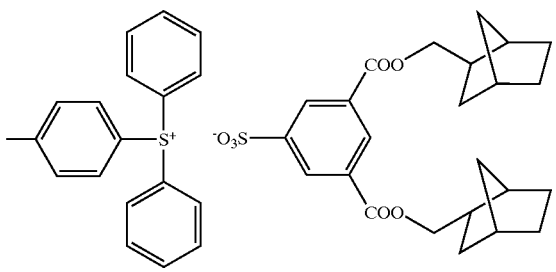

MS (ESI (+) Spectrum): M+ 277.2 MS (ESI (−) Spectrum): M− 461.2

ACID GENERATOR SYNTHESIS EXAMPLE 3

Synthesis of Acid Generator B3

After charging 30.0 parts of 1-adamantanemethanol and 180 parts of toluene into a flask, the mixture was heated to 80° C. To this was added 5-sulfoisophtalic acid, and the mixture was refluxed while dehydration for 6 hours. After cooling, the reaction mixture was charged to 1000 parts of n-heptane, and then stirred at for an hour. The resulting mixture was filtrated and the solid obtained was dried under reduced pressure to obtain 40.0 parts of diester. 39.0 parts of the diester was dissolved in 234 parts of methanol, and to the solution was added 12.5 parts of silver oxide, and the mixture was stirred for 12 hours at room temperature. After filtration, to the filtrate were added 95.0 parts of methanol and 190 parts of chloroform, and further added dropwise the mixture of 23.7 parts of p-tolyldiphenylsulfonium iodide and 237 parts of methanol, and then the mixture was stirred for 12 hours at room temperature. After filtration, to the filtrate was 500 parts of ethyl acetate, and washed with 125 parts of water thrice. The organic layer obtained was filtrated and then concentrated. The concentrate was washed with 300 parts of n-heptane and then concentrated, and the washing and concentration was repeated seven times. The concentrate was washed with another 300 parts of n-heptane and then washed, concentrated completely to obtain 35.7 parts of white crystals.

It was confirmed that the structure of the crystals was the following formula by NMR ("GX-270" manufactured by JEOL Ltd.) and mass spectrometry (LC analyser is No.1100 manufactured by HP, MASS analyser is LC/MSD manufactured by HP).

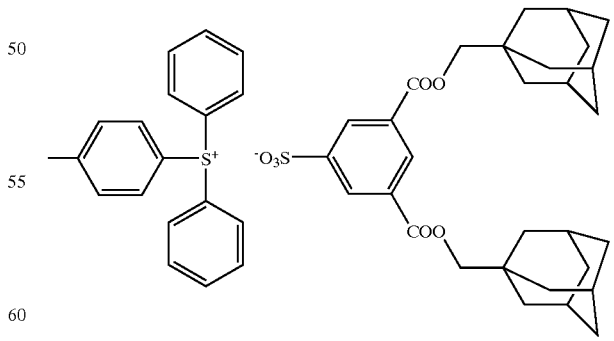

$^1$H-NMR (chloroform-d, internal standard substance: tetramethylsilane): δ (ppm) 1.62–1.75 (m, 24H); 1.98 (brs, 6H); 2.44 (s, 3H); 3.93 (s, 4H); 7.46 (d, 2H); 7.64–7.80 (m, 12H); 8.63 (t, 1H); 8.79 (d, 2H) MS (ESI (+) Spectrum): M+ 277.2 MS (ESI (−) Spectrum): M− 541.2

Intermediate for Acid Generator Synthesis Example (1) After charging 50 parts of 4-chloro-3,5-dinitrobenzoic acid, 0.3 part of 98% sulfuric acid, 78 parts of cyclohexaneethanol and 50 parts of sulfolane into a flask, the mixture was heated to 100 to 110° C., and was maintained at the same temperature for 8 to 10 hours. After checking the disapearance of 4-chloro-3,5-dinitrobenzoic acid by HPLC, the reaction mass was cooled to room temperature under atmospheric pressure, and to the mass was 240 parts of methanol, and was stirred for 30 minutes. The resulting mixture was filtrated to obtain crystals, and the crystals were washed with 40 parts of methanol and then dried to obtain 58 parts of 2-cyclohexylethyl 4-chloro-3,5-dinitrobenzoate.

(2) 50 parts of 2-cyclohexylethyl 4-chloro-3,5-dinitrobenzoate was dissolved in 157 parts of acetonitrile. To the solution was added dropwise the solution of 35.4 parts of sodium sulfite and 72 parts of water at room temperature. To the mixed solution 1965 parts of acetonitrile little by little, and then was added 500 parts of water to obtain uniform solution. The solution was heated to 80° C. and maintained the temperature with stirring for 3 hours. After checking the disapearance of 2-cyclohexylethyl 4-chloro-3,5-dinitrobenzoate by HPLC, the resulting solution was concentrated 80° C. under reduced pressure. To the concentrate was added 80 parts of methanol, and stirred for 30 minutes. The crystals precipitated were filtrated and washed with 40 parts of methanol, and the filtrate was concentrated at 80° C. to obtain yellow crystals. Further, to the crystals was added 400 ml of isopropanol and the mixture was subjected to azeotropic dehydration. The crystals were filtrated and washed with 200 ml of isopropanol, and dried to obtain 42.2 parts of sodium 4-(2-cyclohexylethoxycarbonyl)-2,6-dinitrobenzenesulfonate (Yield:90.7%, Yield:70%).

ACID GENERATOR SYNTHESIS EXAMPLE 4

Synthesis of Acid Generator B4

5.0 parts of sodium 4-(2-cyclohexylethoxycarbonyl)-2,6-dinitrobenzenesulfonate was dissolved in 50.0 parts of water, 50.0 parts of dimethylformamide and 50.0 parts of methanol. To the solution was added mixed solution of 3.5 parts of triphenylsulfonium chloride and 50.0 parts of water. After stirred for 12 hours, the reaction mixture was filtrated, and then the filtrate was concentrated. The concentrate was dissolved in 200 parts of chloroform, the solution was washed with ion-exchanged water, and the organic layer obtained was concentrated. To the concenrate was added 50 parts of tert-butyl methyl ether and washed. The washed concentrate was filtrated and dried under reduced pressure to obtain 3.6 parts of white crystals.

It was confirmed that the structure of the crystals was the following formula by NMR ("GX-270" manufactured by JEOL Ltd.).

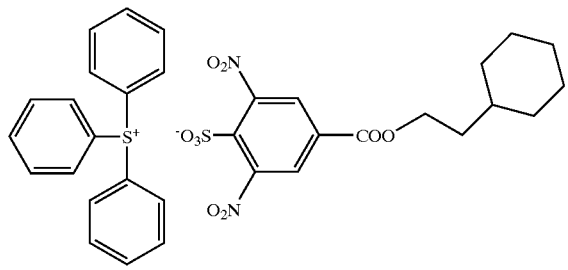

$^1$H-NMR (chloroform-d, internal standard substance: tetramethylsilane): δ (ppm) 0.91–1.03 (m, 2H); 1.13–1.28 (m, 3H); 1.36–1.45 (m, 1H); 1.63–1.80 (m, 7); 4.40 (t, 2H); 7.62–7.78 (m, 15H); 8.17 (d, 2H)

ACID GENERATOR SYNTHESIS EXAMPLE 5

Synthesis of Acid Generator B5

(1) 11.20 parts of sodium 4-(2-cyclohexylethoxycarbonyl)-2,6-dinitrobenzenesulfonate was dissolved in 60.0 parts of ion-exchanged water and 60 parts of methanol. The solution was passed thrice through a column filled with 32.07 parts of ion-exchange resin (Duolite C20 H type, manufactured by Sumitomo Chemical Co., Ltd.). After concentrating to eliminate methanol, the concentrate was freeze-dried to obtain 9.87 parts of 2-cyclohexylethyl 4-sulfo-3,5-dinitrobenzoate.

(2) 3.00 parts of 2-cyclohexylethyl 4-sulfo-3,5-dinitrobenzoate, 50 parts of ion-exchanged water and 30 parts of methanol were charged into four-necked flask. To this was added 0.92 part of silver oxide and the mixture was stirred for 15 hours. After filtration, to the filtrate was added 4.17 parts of tris(4-tert-butylphenyl)sulfonium iodide and 42 parts of methanol, and the mixture was stirred for 15 hours. To the resulting mixture was added 200 parts of chloroform to extract. The mixture was shaked and then settled to give organic phase and aqueous phase. The aqueous phase was extracted with 50 parts of chloroform twice. The organic phases were combined and washed with 60 parts of ion-exchanged water thrice. The washed organic phase was concentrated, and then to the concentrate was added 100 parts of tert-butyl methyl ether to give precipitate. The precipitate was filtered and dried to obtain 5.26 parts of the object compound.

It was confirmed that the structure of the crystals was the following formula by NMR ("GX-270" manufactured by JEOL Ltd.).

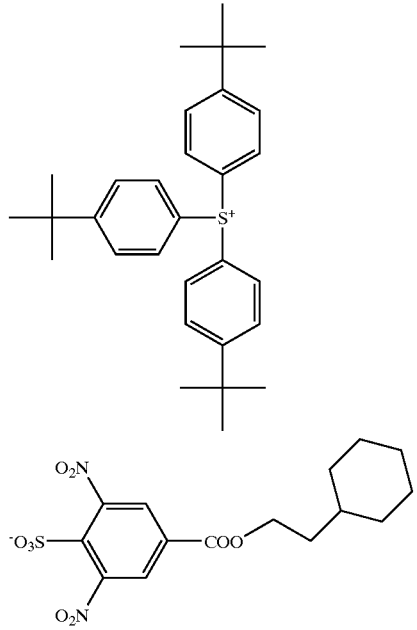

$^1$H-NMR (chloroform-d, internal standard substance: tetramethylsilane): δ (ppm) 0.87–0.99 (m, 2H); 1.09–1.42 (m, 33H); 1.55–1.73 (m, 5H); 4.37 (t, 2H) 7.77–7.85 (m, 12H); 8.35 (s, 2H)

ACID GENERATOR SYNTHESIS EXAMPLE 6

Synthesis of Acid Generator B6

3.50 parts of 2-cyclohexylethyl 4-sulfo-3,5-dinitrobenzoate, 50 parts of ion-exchanged water and 35 parts of methanol were charged into four-necked flask. To this was added 1.07 part of silver oxide and the mixture was stirred for 15 hours. After filtration, to the filtrate was added 3.88 parts of 4-tert-butylphenyldiphenylsulfonium iodide and 20 parts of methanol, and the mixture was stirred for 15 hours. To the resulting mixture was added 200 parts of chloroform to extract. The mixture was shaked and then settled to give organic phase and aqueous phase. The aqueous phase was extracted with 50 parts of chloroform twice. The organic phases were combined and washed with 60 parts of ion-exchanged water thrice. The washed organic phase was concentrated, and then to the concentrate was added 100 parts of tert-butyl methyl ether to give precipitate. The precipitate was filtered and dried to obtain 5.26 parts of the white crystals.

It was confirmed that the structure of the crystals was the following formula by NMR ("GX-270" manufactured by JEOL Ltd.).

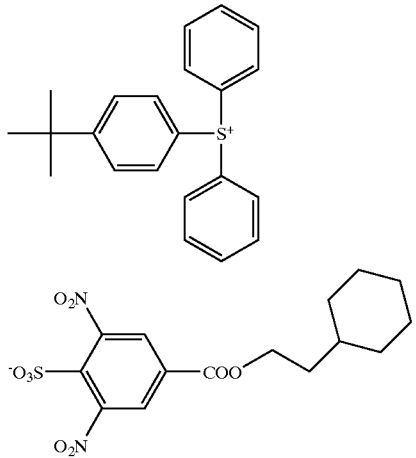

$^1$H-NMR (chloroform-d, internal standard substance: tetramethylsilane): δ (ppm) 0.87–0.99 (m, 2H); 1.10–1.74 (m, 20H); 4.35 (t, 2H); 7.74–7.90 (m, 14H); 8.33 (s, 2H)

ACID GENERATOR SYNTHESIS EXAMPLE 7

Synthesis of Acid Generator C1

The reactions and post treatments were conducted in the same manner as in Acid generator synthesis example 1 except that n-octanol was used instead of cyclohexaneethanol, and yellow oil product was obtained.

It was confirmed that the structure of the oil product was the following formula by NMR ("GX-270" manufactured by JEOL Ltd.) and mass spectrometry (LC analyser is No.1100 manufactured by HP, MASS analyser is LC/MSD manufactured by HP).

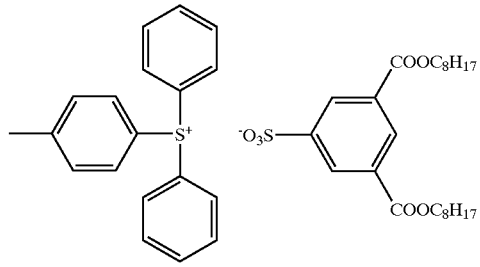

$^1$H-NMR (chloroform-d, internal standard substance: tetramethylsilane): δ (ppm) 0.89 (t, 6H); 1.19–1.39 (m, 20H); 1.72 (dd, 4H); 2.44 (s, 3H); 4.29 (t, 4H); 7.46 (d, 2H); 7.62–7.77 (m, 12H); 8.62 (s, 1H); 8.79 (d, 2H) MS (ESI (+) Spectrum): M+ 277.2 MS (ESI (−) Spectrum): M− 469.2

RESIN SYNTHESIS EXAMPLE 1

Synthesis of Resin A1

2-Ethyl-2-adamantyl methacrylate, 5-methacryloyloxy-2,6-norbornenelactone and α-methacryloyloxy-γ-butyrolactone were charged at a molar ratio of 35:40:25 (12.42 g:12.70 g:5.58 g), and 30.70 g of 1,4-dioxane was added, and then was added 0.70 g of azobisisobutyronitrile as an initiator to prepare solution. In another flask, 46.04 g of 1,4-dioxane was charged and heated to 87° C. To this was added the solution obtained above over one hour and the mixture was stirred for 5 hours maintaining the temperature. Then, operation of pouring into large amount of n-heptane to cause crystallization was repeated three times for purification, and then dried to obtain 25.4 g (Yield: 82.7%) of copolymer having an average molecular weight of 8900. This is called resin A1.

RESIN SYNTHESIS EXAMPLE 2

Synthesis of Resin A2

2-Ethyl-2-adamantyl methacrylate, 3-hydroxy-1-adamantyl methacrylate and α-methacryloyloxy-γ-butyrolactone were charged at a molar ratio of 5:2.5:2.5 (20.0 parts:9.5 parts:7.3 parts), and methyl isobutyl ketone in twice weight based on all monomers was added, to prepare solution. To the solution was added azobisisobutyronitrile as an initiator in a ratio of 2 mol % based on all monomer molar amount, and the mixture was heated at 80° C. for about 8 hours. Then, the reaction solution was poured into large amount of heptane to cause precipitation, and this operation was repeated three times for purification. As a result, copolymer having a weight-average molecular weight of about 9,200 was obtained. This is called resin A2.

As Resin A3, IHM-55-10K (Trade No., the product of Mitsubishi Rayon Co., Ltd., mixture of structural units of MAMA and HGBME each of which structure is shown below, ratio of MAMA/HGBMA=1/1) was used.

HGBMA
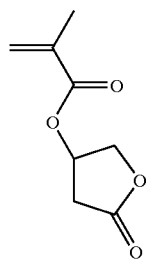
MAMA
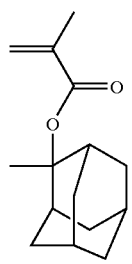
Resist compositions were prepared using raw materials shown below in addition to the resins obtained in the above-mentioned resins.
<Acid generator>
B1:
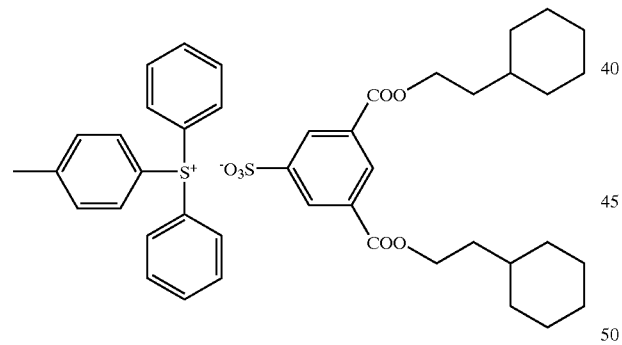
B2:
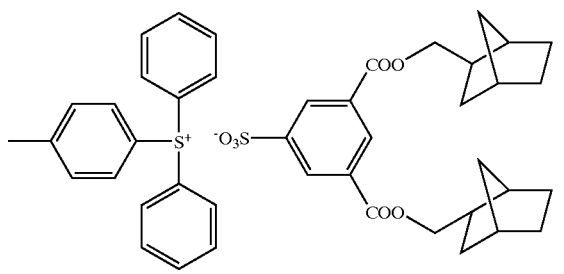
B3:
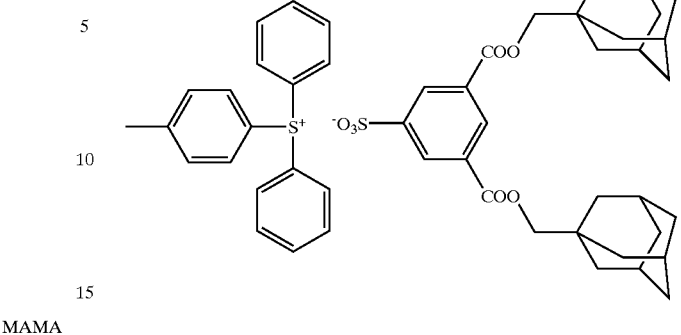
B4:
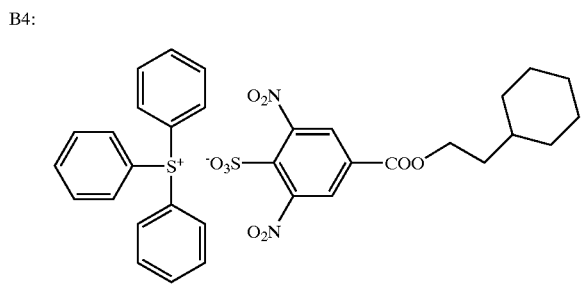
B5:
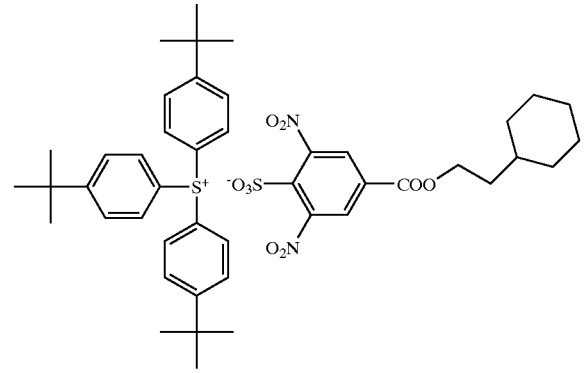
B6:
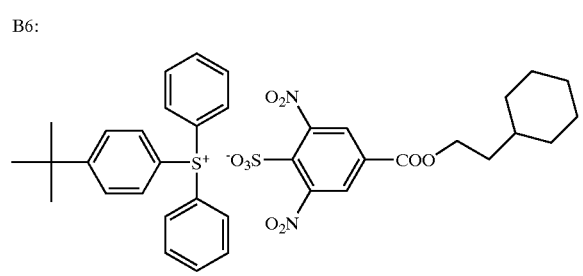

C1:

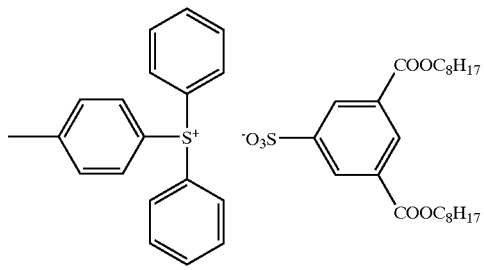

<Quencher>
D1: 2,6-diisopropylaniline

| <Solvent> | |
|---|---|
| E1: propyleneglycol monomethyl ether acetate | 26 parts |
| 2-heptanone | 26 parts |
| γ-butyrolactone | 3 parts |
| E2: propyleneglycol monomethyl ether acetate | 57 parts |
| γ-butyrolactone | 3 parts |

EXAMPLE 1 AND COMPARATIVE EXAMPLE 1

The following components were mixed and dissolved, further, filtrated through a fluorine resin filter having pore diameter of 0.2 μm, to prepare resist liquid.
Resin (Kind and Amount are Described in Table 1)
Acid generator (kind and amount are described in Table 1)
Quencher (kind and amount are described in Table 1)
Solvent (kind and amount are described in Table 1)

Silicon wafers were each coated with "ARC-29A-8", which is an organic anti-reflective coating composition available from Brewer Co., and then baked under the conditions: 215° C., 60 seconds, to form a 780 Å-thick organic anti-reflective coating. Each of the resist liquids prepared as above was spin-coated over the anti-reflective coating so that the thickness of the resulting film became 0.30 μm or 0.25 μm after drying. The silicon wafers thus coated with the respective resist liquids were each prebaked on a direct hotplate at temperature shown in "PB" column in Table 1 for 60 seconds. Using an ArF excimer stepper ("NSR ArF" manufactured by Nicon Corporation, NA=0.55, ⅔ Annular), each wafer thus formed with the respective resist film was subjected to line and space pattern exposure, with the exposure quantity being varied stepwise.

After the exposure, each wafer was subjected to post-exposure baking on a hotplate at temperature shown in "PEB" column in Table 1 for 60 seconds and then to paddle development for 60 seconds with an aqueous solution of 2.38 wt % tetramethylammonium hydroxide.

A bright field pattern developed on the organic anti-reflective coating substrate was observed with a scanning electron microscope, the results of which are shown in Table 2. The term "bright field pattern", as used herein, means a pattern obtained by exposure and development through a reticle comprising an outer frame made of a chromium layer (light-shielding layer) and linear chromium layers (light-shielding layers) formed on a glass surface (light-transmitting portion) extending inside the outer frame. Thus, the bright field pattern is such that, after exposure and development, resist layer surrounding the line and space pattern is removed while resist layer corresponding to the outer frame is left on the outer side of the region from which the resist layer is removed.

Effective sensitivity: It is expressed as the amount of exposure that the line pattern (light-shieldin layer) and the space pattern (light-transmitting layer) become 1:1 after exposure through 0.13 μm line and space pattern mask and development.

Resolution: It is expressed as the minimum size of space pattern which gave the space pattern split by the line pattern at the exposure amount of the effective sensitivity.

Cofiguration of Resist Pattern: Cross-sectional views of resist patterns are evaluated using symbols "×", "○" and "◉", which represent rounded top configuration, slightly rounded top configuration and rectangular top configuration, respectively.

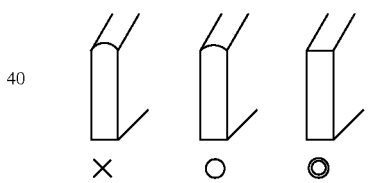

TABLE 1

| Example No. | Resin (Parts) | Acid generator (Part) | Quencher (Part) | Solvent | PB | PEB | Thickness of film |
|---|---|---|---|---|---|---|---|
| Example 1 | A1/10 | B1/0.27 | D1/0.0075 | E1 | 140° C. | 125° C. | 0.30 |
| Example 2 | A1/10 | B3/0.3 | D1/0.0075 | E1 | 140° C. | 125° C. | 0.30 |
| Example 3 | A2/10 | B1/0.27 | D1/0.0075 | E2 | 140° C. | 125° C. | 0.25 |
| Example 4 | A2/10 | B2/0.27 | D1/0.0075 | E2 | 140° C. | 125° C. | 0.25 |
| Example 5 | A2/10 | B3/0.3 | D1/0.0075 | E2 | 140° C. | 130° C. | 0.25 |
| Example 6 | A3/10 | B1/0.27 | D1/0.0075 | E2 | 140° C. | 130° C. | 0.25 |
| Example 7 | A3/10 | B2/0.27 | D1/0.0075 | E2 | 140° C. | 130° C. | 0.25 |
| Example 8 | A3/10 | B3/0.3 | D1/0.0075 | E2 | 140° C. | 130° C. | 0.25 |
| Example 9 | A2/10 | B4/0.24 | D1/0.0075 | E2 | 140° C. | 130° C. | 0.25 |
| Example 10 | A2/10 | B5/0.30 | D1/0.0075 | E2 | 140° C. | 130° C. | 0.25 |
| Example 11 | A2/10 | B6/0.26 | D1/0.0075 | E2 | 140° C. | 130° C. | 0.25 |
| Comparative example 1 | A1/10 | C1/0.27 | D1/0.0075 | E1 | 140° C. | 125° C. | 0.30 |

TABLE 1-continued

| Example No. | Resin (Parts) | Acid generator (Part) | Quencher (Part) | Solvent | PB | PEB | Thickness of film |
|---|---|---|---|---|---|---|---|
| Comparative example 2 | A2/10 | C1/0.27 | D1/0.0075 | E2 | 140° C. | 130° C. | 0.25 |
| Comparative example 3 | A3/10 | C1/0.27 | D1/0.0075 | E2 | 140° C. | 130° C. | 0.25 |

TABLE 2

| Example No. | Effective Sensitivity (mJ/cm$^2$) | Resolution ($\mu$m) | Smoothness of pattern wall surface |
|---|---|---|---|
| Example 1 | 23 | 0.12 | ○ |
| Example 2 | 30 | 0.12 | ◉ |
| Example 3 | 45 | 0.12 | ○ |
| Example 4 | 60 | 0.12 | ○ |
| Example 5 | 75 | 0.12 | ◉ |
| Example 6 | 27.5 | 0.12 | ○ |
| Example 7 | 35 | 0.12 | ○ |
| Example 8 | 45 | 0.11 | ◉ |
| Example 9 | 27 | 0.12 | ◉ |
| Example 10 | 51 | 0.12 | ○ |
| Example 11 | 39 | 0.12 | ◉ |
| Comparative example 1 | 18 | 0.12 | X |
| Comparative example 2 | 33 | 0.12 | X |
| Comparative example 3 | 21 | 0.12 | X |

The sulfonate of the present invention is energy-active, and can be suitably used as a component in a resist. The chemical amplification type positive resist composition of the present invention gives resist patterns having remarkably improved line edge roughness, and also provides excellent resist abilities such as sensitivity, resolution and the like. Therefore, it is suitable for excimer laser lithography using ArF, KrF and the like, has large industrial values.

What is claimed is:

1. A sulfonate of the formula (I):

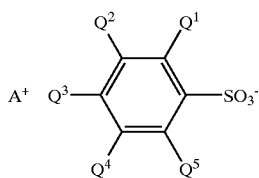

(I)

wherein $Q^1$, $Q^2$, $Q^3$, $Q^4$ and $Q^5$ each independently represent hydrogen, alkyl having 1 to 16 carbon atoms, alkoxy having 1 to 16 carbon atoms, halogen, aryl having 6 to 12 carbon atoms, aralkyl having 7 to 12 carbon atoms, cyano, sulfide, hydroxy, nitro or a group of the formula (I')

—COO—X—Cy$^1$ (I')

wherein X represents alkylene and at least one —CH$_2$— in the alkylene may be substituted by —O— or —S—, and Cy$^1$ represents alicyclic hydrocarbon having 3 to 20 carbon atoms, and A$^+$ represents a counter ion, with the proviso that at least one of $Q^1$, $Q^2$, $Q^3$, $Q^4$ and $Q^5$ is the group of the formula (I').

2. The sulfonate according to claim 1, wherein X in the formula (I') is alkylene.

3. The sulfonate according to claim 1, wherein Cy$^1$ in the formula (I') is cyclohexyl, 2-norbornyl, 1-adamantyl or 2-adamantyl.

4. The sulfonate according to claim 1, wherein A$^+$ is a counter ion of the formula (IIa)

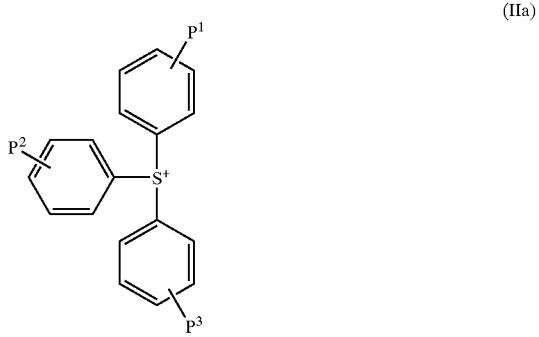

(IIa)

wherein $P^1$, $P^2$ and $P^3$ each independently represent hydrogen, hydroxyl, alkyl having 1 to 6 carbon atoms or alkoxy having 1 to 6 carbon atoms.

5. The sulfonate according to claim 1, wherein A$^+$ is a counter ion of the formula (IIb)

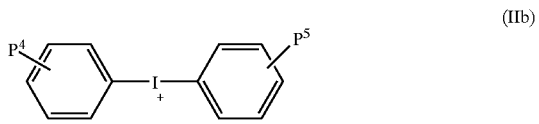

(IIb)

wherein $P^4$ and $P^5$ each independently represent hydrogen, hydroxyl, alkyl having 1 to 6 carbon atoms or alkoxy having 1 to 6 carbon atoms.

6. The sulfonate according to claim 1, wherein A$^+$ is a counter ion of the formula (IIc)

(IIc)

wherein $P^6$ and $P^7$ each independently represent alkyl having 1 to 6 carbon atoms or cycloalkyl having 3 to 10 carbon atoms, or $P^6$ and $P^7$ bond to form divalent acyclic hydrocarbon having 3 to 7 carbon atoms which form a ring together with the adjacent S$^+$, and at least one —CH$_2$— in the divalent acyclic hydrocarbon may be substituted by —CO—, —O— or —S—; $P^8$ represents hydrogen, $P^9$ represents alkyl having 1 to 6 carbon atoms, cycloalkyl having 3 to 10 carbon atoms or aromatic ring group optionally substituted, or $P^8$ and $P^9$ bond to form 2-oxocycloalkyl together with the adjacent —CHCO—.

7. The sulfonate according to claim 1, wherein A$^+$ is a counter ion of the formula (IId)

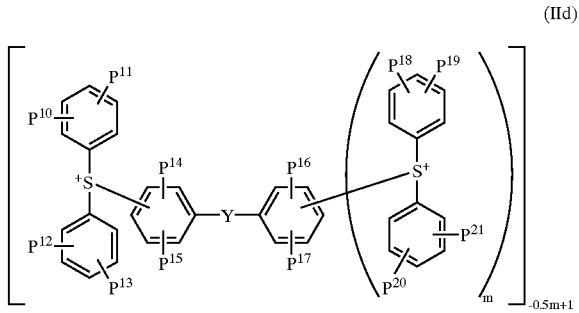

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen, hydroxyl, alkyl having 1 to 6 carbon atoms or alkoxy having 1 to 6 carbon atoms, Y represents sulfur or oxygen, and m represents 0 or 1.

8. A chemical amplification type positive resist composition comprising a sulfonate of the formula (I)

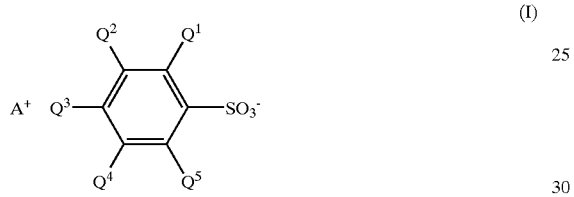

(I)

wherein $Q^1$, $Q^2$, $Q^3$, $Q^4$ and $Q^5$ each independently represent hydrogen, alkyl having 1 to 16 carbon atoms, alkoxy having 1 to 16 carbon atoms, halogen, aryl having 6 to 12 carbon atoms, aralkyl having 7 to 12 carbon atoms, cyano, sulfide, hydroxy, nitro or a group of the formula (I′)

—COO—X—$Cy^1$   (I′)

wherein X represents alkylene and at least one —$CH_2$— in the alkylene may be substituted by —O— or —S—, and $Cy^1$ represents alicyclic hydrocarbon having 3 to 20 carbon atoms, and $A^+$ represents a counter ion, with the proviso that at least one of $Q^1$, $Q^2$, $Q^3$, $Q^4$ and $Q^5$ is the group of the formula (I′); and resin which contains a structural unit having an acid labile group and which itself is insoluble or poorly soluble in an alkali aqueous solution but becomes soluble in an alkali aqueous solution by the action of an acid.

9. The composition according to claim 8 wherein the content of the structural unit having an acid-labile group in all structural units of the resin is from 10 to 80% by mol.

10. The composition according to claim 8 wherein the structural unit having an acid-labile group is a structural unit derived from 2-alkyl-2-adamantyl (meth)acrylate or 1-(1-adamantyl)-1-alkylalkyl(meth)acrylate.

11. The composition according to claim 8 wherein the resin contains, in addition to the structural unit having an acid-labile group, further at least one structural unit selected from the group consisting of a structural unit derived from p-hydroxystyrene, a structural unit derived from m-hydroxystyrene, a structural unit derived from 3-hydroxy-1-adamantyl(meth)acrylate, a structural unit derived from 3,5-dihydroxy-1-adamantyl(meth)acrylate, a structural unit derived from (meth)acryloyloxy-γ-butyrolactone having a lactone ring optionally substituted by alkyl, a structural unit of the formula (VIIa) and a structural unit of the following formula (VIIb)

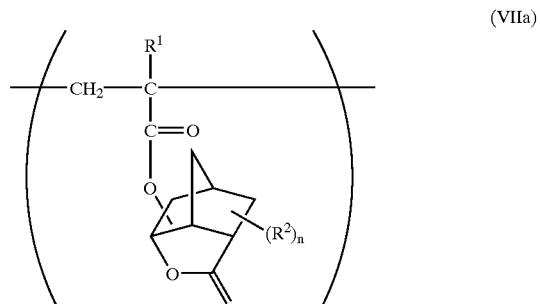

(VIIa)

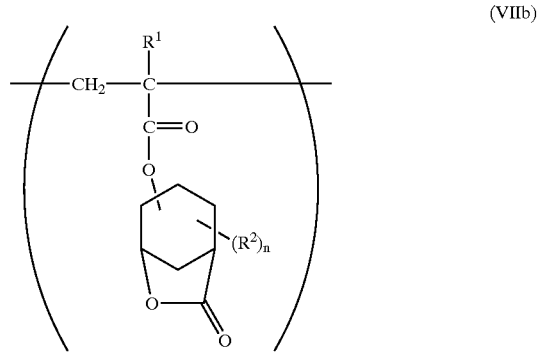

(VIIb)

wherein $R^1$ and $R^2$ each independently represent hydrogen, methyl, trifluoromethyl or, and n represents an integer of 1 to 3.

12. The composition according to claim 9 wherein the resin further contains a structural unit derived from 2-norbornene and a structural unit derived from an aliphatic unsaturated dicarboxylic anhydride.

13. The composition according to claim 8 wherein the composition further comprises basic nitrogen-containing organic compound as a quencher.

14. The composition according to claim 8 wherein the composition further comprises a surfactant.

15. The composition according to claims 8 wherein, in the formula (I), $A^+$ is a counter ion of the formula (IIa), the formula (IIb), the formula (IIc) or the formula (IId):

A counter ion of the formula (IIa)

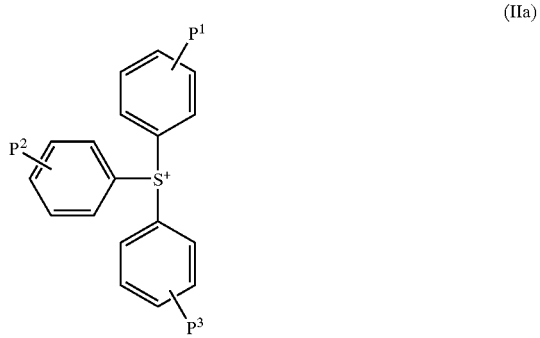

(IIa)

wherein $P^1$, $P^2$ and $P^3$ each independently represent hydrogen, hydroxyl, alkyl having 1 to 6 carbon atoms or alkoxy having 1 to 6 carbon atoms.

A counter ion of the formula (IIb)

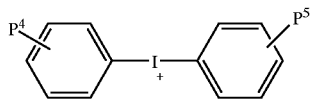
(IIb)

wherein $P^4$ and $P^5$ each independently represent hydrogen, hydroxyl, alkyl having 1 to 6 carbon atoms or alkoxy having 1 to 6 carbon atoms.

A counter ion of the formula (IIc)

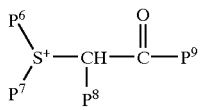
(IIc)

wherein $P^6$ and $P^7$ each independently represent alkyl having 1 to 6 carbon atoms or cycloalkyl having 3 to 10 carbon atoms, or $P^6$ and $P^7$ bond to form divalent acyclic hydrocarbon having 3 to 7 carbon atoms which form a ring together with the adjacent $S^+$, and at least one —$CH_2$— in the divalent acyclic hydrocarbon may be substituted by —CO—, —O— or —S—; $P^8$ represents hydrogen, $P^9$ represents alkyl having 1 to 6 carbon atoms, cycloalkyl having 3 to 10 carbon atoms or aromatic ring group optionally substituted, or $P^8$ and $P^9$ bond to form 2-oxocycloalkyl together with the adjacent —CHCO—.

A counter ion of the formula (IId)

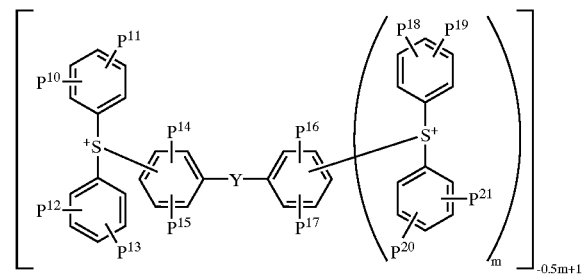
(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent hydrogen, hydroxyl, alkyl having 1 to 6 carbon atoms or alkoxy having 1 to 6 carbon atoms, Y represents sulfur or oxygen, and m represents 0 or 1.

* * * * *